United States Patent
Desai et al.

(10) Patent No.: US 9,777,123 B2
(45) Date of Patent: Oct. 3, 2017

(54) SULFATED BETA-O4 LOW MOLECULAR WEIGHT LIGNINS

(71) Applicant: VIRGINIA COMMONWEALTH UNIVERSITY, Richmond, VA (US)

(72) Inventors: Umesh R. Desai, Glen Allen, VA (US); Jay Thakkar, Denver, CO (US); Akul Mehta, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/889,870

(22) PCT Filed: May 29, 2014

(86) PCT No.: PCT/US2014/039882
§ 371 (c)(1),
(2) Date: Nov. 9, 2015

(87) PCT Pub. No.: WO2014/194015
PCT Pub. Date: Dec. 4, 2014

(65) Prior Publication Data
US 2016/0115280 A1  Apr. 28, 2016

Related U.S. Application Data

(60) Provisional application No. 61/829,042, filed on May 30, 2013.

(51) Int. Cl.
C07G 1/00 (2011.01)
C08H 7/00 (2011.01)
C07C 305/22 (2006.01)

(52) U.S. Cl.
CPC ............. *C08H 6/00* (2013.01); *C07C 305/22* (2013.01)

(58) Field of Classification Search
CPC ................................ C08H 6/00; C07C 305/22
See application file for complete search history.

(56) References Cited

U.S. PATENT DOCUMENTS

| | | | |
|---|---|---|---|
| 8,491,872 B2 * | 7/2013 | Desai | A61K 9/007 424/45 |
| 8,613,909 B2 * | 12/2013 | Desai | A61K 9/007 424/45 |
| 8,993,620 B2 * | 3/2015 | Desai | A61K 9/007 514/469 |
| 2012/0027691 A1 | 2/2012 | Desai et al. | |

FOREIGN PATENT DOCUMENTS

| | | | |
|---|---|---|---|
| EP | 1367141 A1 | 12/2003 | |
| WO | WO 2010027594 A2 * | 3/2010 | ............. A61K 9/007 |

OTHER PUBLICATIONS

Kishimoto, Takao, Yasumitsu Uraki, and Makoto Ubukata. "Chemical synthesis of β-O-4 type artificial lignin." Organic & biomolecular chemistry 4.7 (2006): 1343-1347.*

(Continued)

*Primary Examiner* — Nicholas Hill
(74) *Attorney, Agent, or Firm* — Whitham, Curtis & Cook, P.C.

(57) ABSTRACT

Low molecular weight sulfated beta-O4 lignin (SbO4L) are potent inhibitors of coagulation with high selectivity.

24 Claims, 10 Drawing Sheets

(56) References Cited

OTHER PUBLICATIONS

Henry, Brian L., et al. "A Novel Allosteric Pathway of Thrombin Inhibition Exosite II Mediated Potent Inhibition of Thrombin by Chemo-Enzymatic, Sulfated Dehydropolymers of 4-Hydroxycinnamic Acids." Journal of Biological Chemistry 282.44 (2007): 31891-31899.*

Kishimoto, Takao, Yasumitsu Uraki, and Makoto Ubukata. "Synthesis of β-O-4-type artificial lignin polymers and their analysis by NMR spectroscopy." Organic & biomolecular chemistry 6.16 (2008): 2982-2987.*

Henry, Brian L., et al. "Interaction of Antithrombin with Sulfated, Low Molecular Weight Lignins Opportunities for Potent, Selective Modulation of Antithrombin Function." Journal of Biological Chemistry 284.31 (2009): 20897-20908.*

Marques, A. P., et al. "Structure of lignosulphonates from acidic magnesium-based sulphite pulping of *Eucalyptus globulus*." Journal of wood chemistry and technology 29.4 (2009): 337-357.*

Saluja, Bhawana, et al. "Novel low molecular weight lignins as potential anti-emphysema agents: in vitro triple inhibitory activity against elastase, oxidation and inflammation." Pulmonary pharmacology & therapeutics 26.2 (2013): 296-304.*

Mehta, Akul Y., et al. "Targeting the GPIbα binding site of thrombin to simultaneously induce dual anticoagulant and antiplatelet effects." Journal of medicinal chemistry 57.7 (2014): 3030-3039.*

Henry et al., "Sulfated, low molecular weight lignins inhibit a select group of heparin-binding serine proteases", Biochemical and Biophysical Research Communications, 2012, pp. 382-386, vol. 417, No. 1.

Henry et al, "Sulfated, low molecular weight lignins are potent inhibitors of plasmin, in addition to thrombin and factor Xa: Novel opportunity for controlling complex pathogens", Thrombosis and Haemostasis, 2010, pp. 507-515, vol. 103, No. 3.

Raghuraman et al., "Viral inhibition studies on sulfated lignin, a chemically modified biopolymer and a potential mimic of heparan sulfate", Biomacromolecules, 2007, pp. 1759-1763, vol. 8, No. 5.

* cited by examiner

Figure. 9 Human whole blood clotting parameters of SbO4L by hemostasis analysis and thromboelastography.

| | | Hemostasis Analysis[a] | | | Thromboelastography[b] | | | | |
|---|---|---|---|---|---|---|---|---|---|
| | [Conc] ($\mu g/ml$) | $TOT^a$ (min) | $PCF^a$ (kDynes) | $CEM^a$ (kDynes/cm²) | [Conc] ($\mu g/ml$) | $R^b$ (min) | $a^b$ (degs) | $MA^b$ (mm) | $G^b$ (kDynes/cm²) |
| SbO4L | 0 | 6.3 | 8.0 | 18.3 | 0 | 7.7 | 56.0 | 61.0 | 7821 |
| | 0.07 | 5.1 | 7.3 | 12.0 | 0.15 | 8.9 | 50.5 | 50.5 | 7658 |
| | 7.4 | 6.6 | 5.8 | 6.3 | 15.2 | 13.2 | 42.5 | 57.0 | 6628 |
| | 37 | 11.3 | 3.3 | 3.9 | 76.5 | 16.9 | 43.0 | 55.5 | 6236 |
| | 74 | 13.6 | 0.7 | 0.6 | 152 | 25.9 | 22.0 | 41.5 | 3547 |
| Enoxaparin | 0 | 3.6 | 7.6 | 21.6 | 0 | 7.0 | 59.0 | 56.5 | 6457 |
| | 0.7 | 5.2 | 5.3 | 15.1 | 1.35 | 8.0 | 49.0 | 51.0 | 5204 |
| | 1.0 | 9.1 | 3.6 | 12.7 | 2.7 | 11.5 | 43.0 | 47.0 | 4434 |
| | 1.6 | 11.0 | 2.8 | 8.5 | 3.4 | 14.0 | 41.0 | 46.0 | 4260 |
| | 2.0 | 12.5 | 0.9 | 2.9 | 4.5 | 17.0 | 31.5 | 42.0 | 3621 |

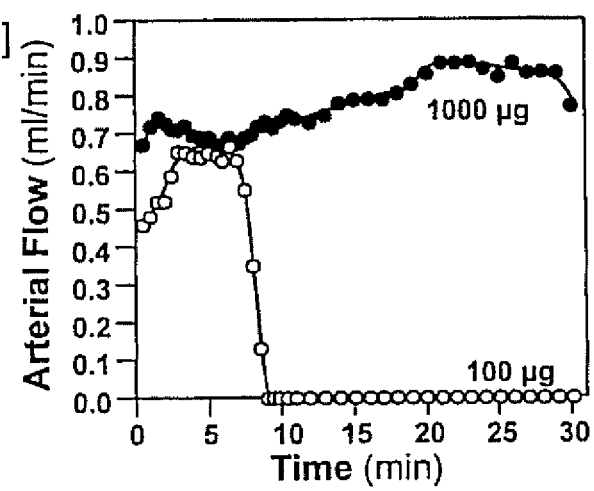
Figure 10A]
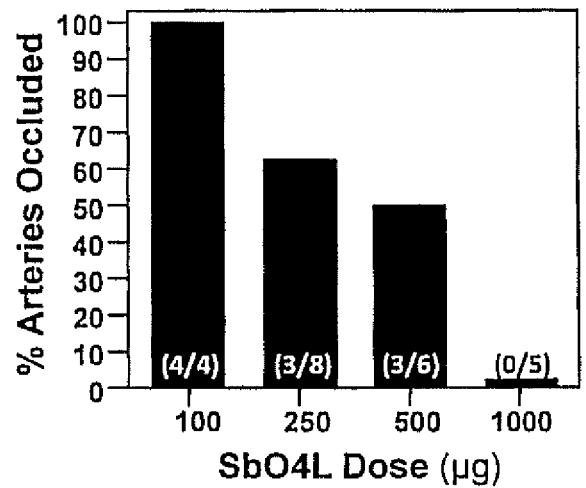
Figure 10B]

SULFATED BETA-O4 LOW MOLECULAR WEIGHT LIGNINS

BACKGROUND

Field of the Invention

This invention is related to a class of synthetic sulfated beta-O4 low molecular weight lignins which are inexpensive to prepare and which have been found to have potent anticoagulation properties in human plasma and whole blood.

Background of the Invention

Heparin (also known as unfractionated heparin (UFH)) is extensively used in the clinic as anticoagulant.[1] UFH is obtained from pig intestinal or lung mucosa and is relatively inexpensive. It is then processed to produce low molecular weight heparins (LMWHs), which are also powerful anticoagulants. Enoxaparin is one such LMWH and is obtained from UFH by chemical treatment. Other LMWHs available in the clinic are obtained from UFH either through chemical or enzymatic means.

Both UFH and LMWHs are used to treat numerous thrombotic disorders including deep-vein thrombosis (DVT), disseminated intravascular coagulations (DIC), pulmonary embolism (PE), acute myocardial infarction, unstable angina and cerebrovascular thrombosis.[1-3] These are also used during surgery, organ transplantation and for extracorporeal bypass procedures. Combined the annual market of heparins is more than $8 billion within the USA alone.

Yet, both heparins have their own disadvantages. Both agents are heterogeneous mixtures of highly sulfated polysaccharide chains, which introduce a number of issues. The biggest drawback is of significant risk of internal bleeding, which might be of either minor bleed or major bleed type. UFH, and sometimes LMWH, is associated with the occurrence of thrombocytopenia in about 3% of patients.[4] Osteoporosis could also arise in some patients upon prolonged heparin usage. In addition to these adverse effects, heparin usage is problematic from quality control and administration perspective. Both UFH and LMWHs possess significant structural variability, which affects their bioavailability and pharmacokinetic parameters. Thus, patient response variability is high. It is also difficult to ascertain the absence of non-heparin-like molecules in a preparation of heparin, e.g., chondroitin sulfate in heparin, because of their structural similarity and mode of preparation. Events of 2008, wherein contamination of UFH by oversulfated chondroitin sulfate led to the death of 81 people in the US, demonstrate the difficulty of quality control with these highly heterogeneous preparations.[5]

It would be advantageous to identify new anticoagulants which possess heparin-like activity without the heterogeneity present in UFH and LMWHs. Further, new anticoagulants, particularly which can be obtained through inexpensive route so as to compete with the cost of UFH therapy, will provide useful alternatives for a number of clinical and other applications.

SUMMARY

Embodiments of the invention relate to sulfated beta-O4 low molecular weight lignin (SbO4L), an oligomer which may be prepared using a fully chemical system and possessing highly specific and potent thrombin inhibitory activity. SbO4L has excellent human plasma and blood anticoagulant potential. SbO4L is an oligomeric lignin molecule that contains only one type of inter-monomeric residue linkage i.e. the β-O-4 linkage. This reduces heterogeneity dramatically so much so that the agent can be assessed for purity using, for example, standard chromatographic tools. The anticoagulant is easily prepared in few simple steps, and thus the new anticoagulant may be inexpensive. Further, industrial scale preparation of SbO4Ls should be possible, thereby increasing its utility. The new anticoagulants described herein should have significant clinical applications.

According to embodiments of the invention, there is described a generic sulfated beta-O4 lignin (SbO4L) scaffold for a family of lignin compounds. These lignin compounds are of low molecular weight (e.g., Molecular Weight ranging from 5000 to 15000 (or 8000 to 12000)). SbO4L has the general chemical structure:

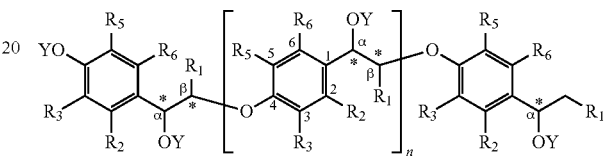

where $Y=SO_3M$ ($M=Na^+$, $Ca^{2+}$, $NH_4^+$ and other equivalent positively charged ions) or H;

n can be 0-50 (e.g., 4-6, 5-10, 5-25, 10-25, 15-25, 10-20, 15-50 as well as other ranges therebetween);

$R_1=CH_2OY$;

$R_2$, $R_3$, $R_5$, and $R_6$ can be hydrogen (—H), C1-10 linear alkyl (e.g., —$CH_3$, —$CH_2CH_3$, etc.), C1-10 branched alkyl (e.g., —$CH(CH_3)_2$, —$CH_2CH(CH_3)_2$, etc.), C1-10 and O1-10 oxyalkyl (e.g., —$OCH_3$, —$OCH_2OCH_3$, etc.), electron-donating (e.g., —OH, —OR (R=C1-10 alkyl, aryl, allyl, and benzyl), —$NH_2$, —NHR (R=C1-10 alkyl, aryl, allyl, and benzyl), electron-withdrawing (e.g., —$NO_2$, —$SO_3H$, —$SO_3M$ ($M=Na^+$, $Ca^{2+}$, $NH_4^+$ and other equivalent positively charged ions) or halogens (—F, —Br, —Cl and —I), and can be the same or different; and chiral centers denoted by (*) are either R or S, and can be the same or different.

Examples of SbO4L ligands include tetrameric-hexameric molecules and decameric-pentadecameric molecules represented by the following generalized structures:

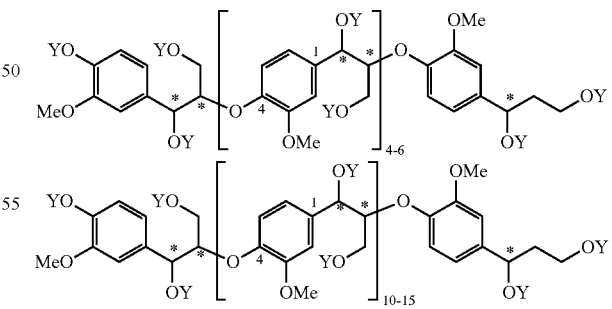

In each of the two exemplary SbO4L families of compounds above, Y is preferably H or $SO_3Na$.

In particular embodiments, mixtures are provided wherein the mixtures contain two or more different sulfated lignin scaffolds, each of which has the generic SbO4L scaffold. For example, the two or more different sulfated lignin scaffolds could have different sizes or have different constituents (i.e., $R_2$, $R_3$, $R_5$ or $R_6$ differ between successive aromatic units), etc. (e.g., different lignins in a mixture could have varying numbers of repeats (n) or one or more different substitutions (e.g., different charged ions, different moieties, such as aryl, alkyl, allyl, oxyalkyl, etc.).

In other embodiments, compositions are provided which including one or more carriers or matrices mixed with one or more sulfated lignins, wherein at least one of the sulfated lignins has the generic SbO4L scaffold. In some compositions, mixtures of two or more different sulfated lignins, where each sulfated lignin has the generic SbO4L scaffold. In some compositions, at least one carrier which is a pharmaceutically acceptable liquid (e.g., saline, oil, water (deionized, distilled, etc.), etc.) is included in the composition. In some compositions, at least one matrix which is a pharmaceutically acceptable sold (e.g. cornstarch, etc.) is included in the composition.

In still other embodiments, methods of producing sulfated lignins with the generic SbO4L scaffold are disclosed. In particular embodiments, a simple three step process of polymerization, reduction, and sulfation is used.

In further embodiments, methods of using sulfated lignins with the generic SbO4L scaffold are disclosed. Exemplary embodiments include using the sulfated lignins, or mixtures, or compositions thereof as an anticoagulant (e.g., through direct, allosteric inhibition of clotting enzymes) and in any application where UFH and LMW may be employed.

DESCRIPTION OF THE DRAWINGS

FIG. 9. Tabular data showing human whole blood clotting parameters of SbO4L by hemostasis analysis and thromboelastography.[a] Analysis was performed using Hemostasis Analysis System (HAS) on human whole blood. Parameters deduced from this analysis included TOT (thrombin onset time), PCF (platelet contractile force) and CEM (clot elastic modulus).[b] Analysis was performed using thromboelastography (TEG) on human whole blood as described in 'Experimental Procedures'. Parameters deduced from this analysis included R (time to clot initiation), α(angle), MA (maximum amplitude) and G (shear elastic modulus).

FIG. 10. A) shows the formation of occlusive platelet-rich thrombus in the carotid artery of mice using a 3.5% $FeCl_3$ solution with two doses of SbO4L, i.e. 100 µg and 1,000 µg. B) demonstrates a dose-dependent decrease in coagulation with a complete inhibition of clot formation at a dose of 1,000 µg of SbO4L. The number shown in brackets shows the fraction of mice which showed complete thrombotic plug formation.

DETAILED DESCRIPTION

Figure 1:
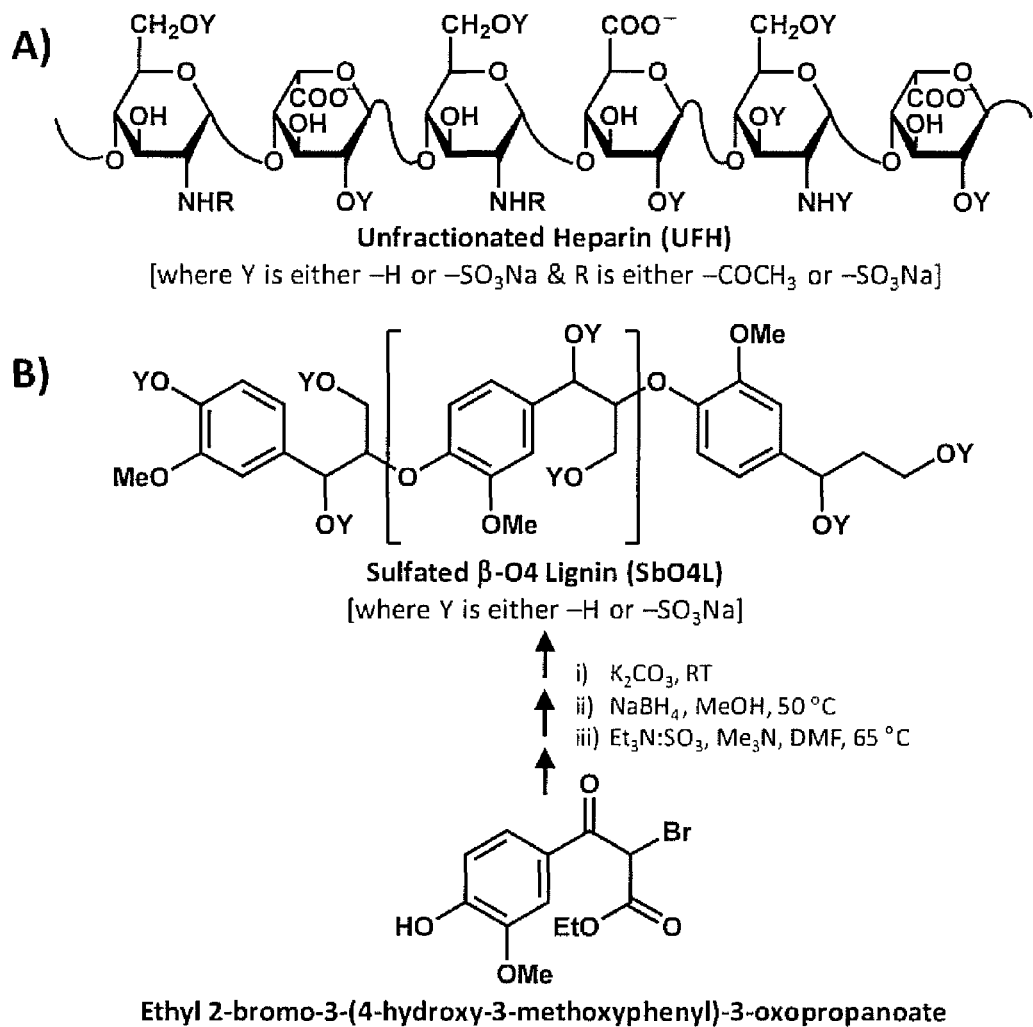
FIG. 1. Structures of unfractionated heparin (UFH) (A) and sulfated β-O4 lignin (SbO4L) (B). Clinically used UFH (and LMW heparins) are a polydisperse mixture of large number of sulfated polysaccharide chains with variations in Y and R groups (shown in A) UFH is prepared from pig mucosa, while LMW heparins are prepared from UFH. SbO4L (B) was synthesized in high yields in three simple steps—alkaline polymerization using $K_2CO_3$ (step i), sodium borohydride reduction of carbonyl groups (step ii) and sulfation of available hydroxyl groups (step iii)—from ethyl 2-bromo-3-(4-hydroxy-3-methoxyphenyl)-3-oxopropanoate monomer.

The invention is related to a family of low molecular weight lignin compounds (e.g., MW ranging from 5000 to 15000) defined by a generic sulfated beta-O4 lignin (SbO4L) scaffold having the general chemical structure:

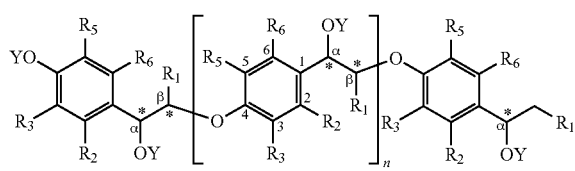

where Y=$SO_3M$ (M=$Na^+$, $Ca^{2+}$, $NH_4^+$ and other equivalent positively charged ions) or H;

n can be 0-50 (e.g., 4-6, 5-10, 5-25, 10-25, 15-25, 10-20, 15-50 as well as other ranges therebetween);

$R_1$=$CH_2OY$;

$R_2$, $R_3$, $R_5$, and $R_6$ can be hydrogen (—H), C1-10 linear alkyl (e.g., —$CH_3$, —$CH_2CH_3$, etc.), C1-10 branched alkyl (e.g., —CH($CH_3$)$_2$, —$CH_2CH(CH_3)_2$, etc.), C1-10 and O1-10 oxyalkyl (e.g., —$OCH_3$, —$OCH_2OCH_3$, etc.), electron-donating (e.g., —OH, —OR (R=C1-10 alkyl, aryl, allyl, and benzyl), —$NH_2$, —NHR (R=C1-10 alkyl, aryl, allyl, and benzyl), electron-withdrawing (e.g., —$NO_2$, —$SO_3H$, —$SO_3M$ (M=$Na^+$, $Ca^{2+}$, $NH_4^+$ and other equivalent positively charged ions) or halogens (—F, —Br, —Cl and —I), and can be the same or different; and chiral centers denoted by (*) are either R or S, and can be the same or different.

The low molecular weight sulfated beta-O4 lignin(s) (SbO4L) are oligomer(s) which can be prepared using a fully chemical system and they possess highly specific and potent thrombin inhibitory activity. Hence, SbO4L lignins have excellent human plasma and blood anticoagulant potential. A defining feature is that SbO4L is an oligomeric lignin molecule that contains only one type of inter-monomeric residue linkage i.e. the β-O-4 linkage. This reduces heterogeneity dramatically, so much so that the agent can be assessed for purity using standard chromatographic tools. The anticoagulant is easily prepared in few simple steps, suggesting that the new anticoagulant is likely to be inexpensive. Further, industrial scale preparation of SbO4Ls is possible, thereby increasing its utility.

The synthesis of the SbO4Ls can be achieved in three easy steps using, for example, alpha-bromo-1,3-ketoester and aryl phenol. The first step involves the polymerization step utilizing a base such as potassium carbonate.

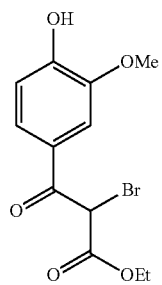

1

↓ $K_2CO_3$ DMF, RT

-continued

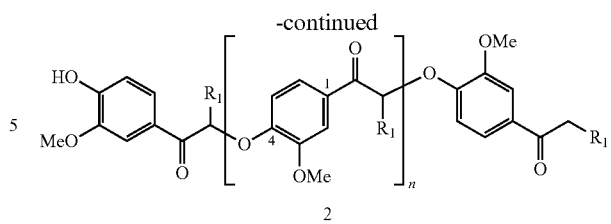

2

Example of Polymerization: In a flask containing the monomer ethyl 2-bromo-3-(4-hydroxy-3-methoxyphenyl)-3-oxopropanoate (0.97 g) (1) (or other appropriate monomer) in anhydrous DMF (5 mL), anhydrous $K_2CO_3$ (0.58 g) was added and stirred under nitrogen. After 24 h the reaction mixture was poured onto ice-water mixture (120 ml) and the pH adjusted to ~2.5 with 2M HCl. The precipitated polymer (2) was filtered, washed with water and lyophilized to remove moisture. In the Example of Polymerization $R_1$=—COOEt.

NMR characterization showed the following corresponding broad peaks for $^1$H-NMR (DMSO-d6): 7.46-7.78 (C2-H and C5-H), 6.91-7.14 (Cβ-H), 6.52-6.66 (C6-H), 4.19-4.20 (—OCH2CH3), 3.79-3.81 (—OCH3), 1.12-1.22 (—OCH2CH3).

$^{13}$C-NMR (DMSO-d6) 188.53, 189.08 (Cα), 165.81, 166.02 (Cγ), 153.16, 150.93, 149.48, 149.01, 147.64, 128.33, 125.51, 124.75, 123.73, 115.17, 114.08, 113.91, 113.09, 112.51, 112.30 (aromatic carbons), 78.54, 78.37 (Cβ), 61.80, 61.67 (—OCH2CH3), 55.78, 55.58 (—OCH3), 13.77 (—OCH2CH3).

After polymerization, the second step is a reduction of the polymer which can be achieved with methanol.

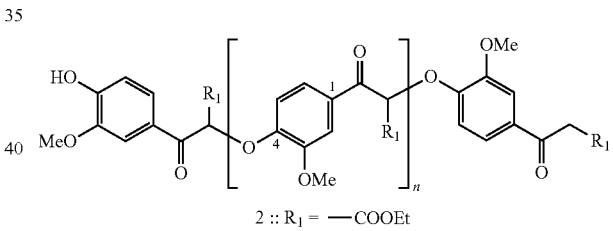

2 :: $R_1$ = —COOEt

↓ NaBH$_4$, MeOH, 50° C.

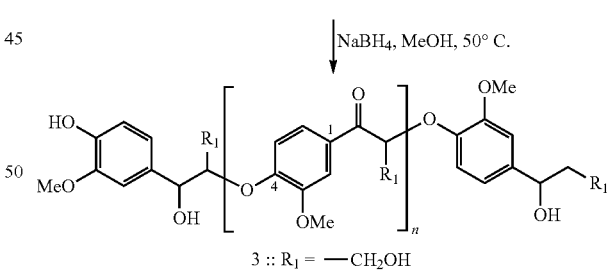

3 :: $R_1$ = —CH$_2$OH

Example of Reduction: The solid (600 mg) (2) was suspended in methanol (10 ml) at 50° C. followed by careful addition of NaBH$_4$ (683 mg) while maintaining 50° C. The mixture gradually turned into a clear solution, which was stirred for 24 h. The solution was then neutralized with acetic acid and poured into 0.5M HCl (200 mL) to precipitate the reduced polymer, which was isolated by centrifugation, washed with water and lyophilized. Dissolution and preferential precipitation using 1,4-dioxane and diethyl ether helped remove low molecular weight chains of the polymer and precipitate the high molecular weight chains. The precipitate (3) was filtered and dried using vacuum.

NMR characterization showed the following corresponding broad peaks for $^1$H-NMR (DMSO-d$_6$): 4.75 (Cα-H), 4.28 (Cβ-H), 3.20-3.71 (Cγ-H and —OC$\underline{H}_3$), 7.02 (C2-H), 6.94 (C5-H), 6.85 (C6-H).

$^{13}$C-NMR (DMSO-d$_6$): 70.8, 71.4 (Cα), 83.6, 84.4 (Cβ), 59.8, 59.9 (Cγ), 55.4 (—O$\underline{C}$H$_3$), 134.7-135.0 (C1), 111.3-111.7 (C2), 148.9 (C3), 146.7-147.0 (C4), 114.5-115.0 (C5), 119.4-119.7 (C6).

The final step is sulfation of the free hydroxy groups.

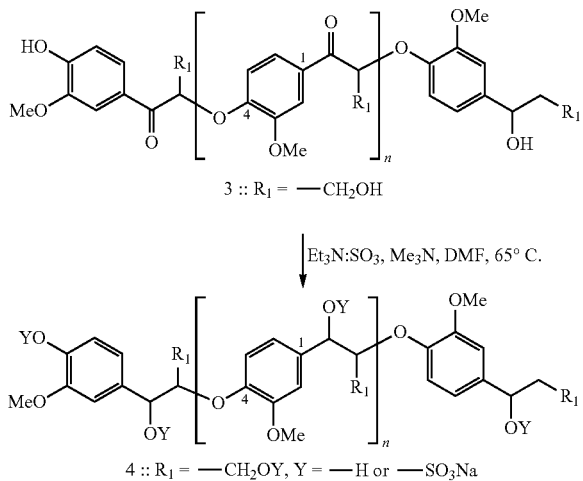

Example of Sulfation: The reduced polymer (50 mg) (3) so obtained was made to react with triethylamine-sulfur trioxide complex (200 mg) in anhydrous DMF (5 ml) at 65° C. for 24 h under reflux. Following the reaction, 30% (w/v) aqueous sodium acetate (35 ml) was added and the mixture stirred overnight. The solution was then poured into ice-cold ethanol (100 ml) to precipitate crude SbO4L LMWL, which was filtered and washed twice with ice-cold ethanol (10 ml each). The recovered solid was desalted using FloatALyzer G2 (Spectrum Labs) dialysis tubes (MWCO 0.1-0.5 KDa). Lyophilization of the dialyzed solution gave SbO4L (4). NMR characterization showed the following corresponding broad peaks for $^1$H-NMR (DMSO-d6): 6.77 (aromatic protons), 3.47-4.27 (Cα-H, Cβ-H, Cγ-H, —OCH$_3$).

$^{13}$C-NMR could not give sufficient signal even at high concentrations of the sample, possibly due to the presence of a wide variety of sulfation patterns and molecules of different chain lengths.

The final step in the exemplary synthesis procedure is sulfation of the free hydroxy groups. Purification of the final product can be performed by either aqueous dialysis or by ultrafiltration. The SbO4L so synthesized was studied for thrombin, factor Xa, factor IXa, factor XIa, factor VIIa and factor XIIa inhibition and found to exhibit potent inhibition of thrombin alone. It prevented human plasma and whole blood clotting at pharmaceutically relevant concentrations and was active in in vivo models.

The molecular weight of the SbO4Ls is low and can range from 5000-15000 Dalton and may be more precisely controlled to e.g., 8000 to 12,000 Da, or 9000±500 Da. For exemplary purposes with regarding molecular weight measurements, gel permeation chromatography (GPC) of SbO4L using Phenogel 5 micron (Phenomenex, Torrance, Calif., 7.6 mm i.d.×300 mm) column and 0.1 N NaOH mobile phase was performed at a constant flow rate of 0.7 mL/min and gave a characteristic broad elution profile by monitoring absorbance at 254 nm. Polystyrene standards of different molecular weights and ferulic acid were used for calibration purposes. The relationship between logarithm of the molecular weight and the elution volume (V) of the standards was found to be linear with a correlation coefficient of 0.99. The SbO4L chromatogram was sliced into 1000 time periods providing 1000 average molecular weights with their corresponding absorbances. These values were used to calculate $M_W$, $M_N$, and $M_P$ values. The molecular weight of the final sulfated lignins were measured using aqueous phase GPC-HPLC and found to have a number average molecular weight $M_N$ of 9,200 Da and weight average molecular weight $M_W$ of 12,300 Da. This procedure is similar to that used earlier for sulfated low molecular weight lignins.

As demonstrated below, the SbO4L compounds, or mixtures thereof, may be useful as an anticoagulant either in vitro, ex vivo or in vivo. They appear to act direct, allosteric inhibition of clotting enzymes. These SbO4L lignin compounds may be combined with a pharmaceutical carrier. In some formulations, the SbO4L lignins can be the same or different. In some formulations, the SbO4L lignins can be combined with other lignins or other selected materials. Suitable pharmaceutically acceptable carriers are known to those of skill in the art. Typically, such compositions are prepared either as liquid solutions or suspensions, however solid forms such as tablets, pills, powders and the like are also contemplated. Solid forms suitable for solution in, or suspension in, liquids prior to administration for in vivo applications, or for addition to blood or plasma in in vivo, in vitro, and ex vivo applications may also be prepared. The preparation (e.g., a composition containing one or more SbO4L compounds) may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of SbO4L in the formulations may vary. However, in general, the amount in the formulations will be from about 1 to about 99% by weight, (e.g., 5% or 10% to 20%, 30%, 40%, 50%, or 60% of one or more SbO4L compounds with the remainder being pharmaceutical carriers, excipients and/or other ingredients).

The SbO4L compositions can be added directly to blood or plasma in an in vitro or ex vivo application.

For in vivo applications, the SbO4L compositions (preparations) may be administered by any of the many suitable means which are well known to those of skill in the art, including but not limited to by injection, inhalation, orally, intranasally, by ingestion of a food product containing the antagonist, topically, as eye drops, via sprays, etc. In preferred anticoagulant embodiments, the mode of administration may be intravenous provisioning or topical application. In addition, the compositions may be administered in conjunction with other treatment modalities such as other medicaments, other types of therapy, and the like.

The amount of SbO4L that is administered to an individual in an in vivo application (who is usually a mammal, typically a human) will vary based on several factors, as will be understood by those of skill in the art. For example, the dose and frequency of administration may vary according to the gender, age, weight, general physical condition, ethnic background, etc. of the individual, as well as whether or not the individual has other diseases or conditions that might impinge on the treatment. Generally, the dose will be in the range of from about 0.01 to about 10000 mg/kg of body weight (e.g., 1 to 50, 100, 250 or 500 mg/kg, etc.).

Exemplary applications of the SbO4L lignins include, but are not limited to 1) as anticoagulant and/or antithrombotic agents in cardiovascular disease therapy; 2) as anti-HSV-1, anti-HSV-2, and anti-HIV-1 agents; 3) as agents against other viruses include dengue, varicella, etc.; 4) as regulators of angiogenesis with implications in cancer; 5) regulator of stem cell growth (either inhibition or proliferation). Their anticoagulant activity can be mediated by already available antidote protamine which is FDA approved for heparin toxicity. SbO4L compounds are less heterogeneous than heparin and low molecular weight heparins. SbO4L compounds are potent inhibitors of coagulation with high selectivity. Mechanistically, they possess novel mode of action and thus are radically different from all known anticoagulants. The SbO4L are readily synthesized, and are not isolated from animal sources and hence less prone to prion borne diseases.

EXAMPLES

A Non-Saccharide, Synthetic Heparin Mimetic that Exhibits Potent Plasma and Blood Anticoagulation Through Selective, Direct and Allosteric Thrombin Inhibition Abstract Sulfated low molecular weight (LMW) lignins which are non-saccharide mimetics of LMW heparins exhibit potent plasma and blood anticoagulation through direct, allosteric inhibition of clotting enzymes. Sulfated β-O4 lignin (SbO4L) is an advanced molecule that is easily synthesized in only three steps and is homogeneous in terms of inter-monomer linkages. SbO4L was found to potently inhibit human thrombin and plasmin ($IC_{50}$=15-34 nM), while related coagulation factors or heparin-binding serine proteases were inhibited with orders of magnitude weaker potency. Plasma antithrombin did not affect SbO4L inhibition of thrombin, while activation of protein C by thrombin-thrombomodulin complex was inhibited with 20-times poorer potency by SbO4L. Kinetic studies showed reduction in maximal rate of substrate hydrolysis, but not in Michaelis constant, indicating a direct allosteric mechanism of action. Competitive inhibition studies suggested that SbO4L interacted with heparin-binding exosite 2 of thrombin. Human plasma and whole blood coagulation assays showed that SbO4L's anticoagulation effect was comparable to that observed with a clinically used LMW heparin. Protamine rapidly and quantitatively reversed SbO4L inhibition of thrombin. Overall, SbO4L is a non-polysaccharide, non-animal derived, very readily synthesizable, thrombin-selective, direct allosteric anticoagulant that can truly challenge the wide-spread clinical use of heparins.

Introduction

Thrombotic disorders such as pulmonary embolism, deep vein thrombosis, and disseminated intravascular coagulation are a major cause of mortality in humans. Heparin and warfarin, two key anticoagulants that treat pro-thrombotic conditions, were discovered in the first half of the 20$^{th}$ century and are still used in essentially the same form.[1] Yet, both suffer from serious bleeding risks and adverse reactions.[1-5] Low molecular weight (LMW) heparins have a better safety profile, but are not devoid of bleeding events.[4,6] Clinical data collected over the past decade shows that newer agents introduced in the clinic including bivalirudin, argatroban, and fondaparinux do not significantly improve anticoagulation therapy over heparins,[7-9] while initial indications with the recently introduced drug, dabigatran, are that it too suffers from bleeding issues.[10,11] Ximelagatran, introduced in 2003, had to be quickly withdrawn because of significant hepatotoxicity. Initial reports with rivaroxaban, introduced in Europe in 2008 and in the US in July 2011, indicate significant benefit with some bleeding risks, but a conclusive statement on its safety record will take time.[12,13]

Mechanistically, anticoagulants can be either active site- or allosteric site-targeting agents. Examples of the enzyme active site inhibitor class include argatroban, melagatran, rivaroxaban, DX9065a, apixaban, and numerous others in various stages of clinical trials. In contrast, no molecule has been introduced in the clinic that inhibits a coagulation enzyme on an exclusively allosteric basis.

Allosteric regulation of coagulation enzyme's function offers a couple of major advantages. Allosterism offers the possibility of fine control over an enzyme's activity. Whereas the efficacy of competitive inhibitors is typically 100%, that for allosteric inhibitors may be tunable so as to achieve 'regulation', i.e., less than quantitative inhibition.[14,15] In principle, allosteric thrombin regulation can strike a delicate balance between pro- and anti-coagulant activities. Allosteric regulation can also better realize specificity of function. Coagulation enzymes are all trypsin-like, homologous enzymes with considerable similarity in their active site geometry.[16] In contrast, significantly greater differences are found in their exosite geometries. For example, exosite 2 of thrombin, which binds heparin, bears some homology to a corresponding site in factor Xa, but display little correspondence to similar sites in factors IXa and XIa.[17] In effect, allosteric regulation promises exquisite control over both specificity of recognition and efficacy of inhibition.

Recently, our laboratory designed the first few examples of exclusively allosteric coagulation enzyme inhibitors. These include the sulfated LMW lignins and sulfated benzofurans.[17-22] Sulfated LMW lignins were originally designed to mimic the allosteric interaction of heparin with antithrombin, a key regulator of coagulation.[23,24] Yet, detailed studies pointed to direct inhibition of thrombin, factor Xa and factor XIa as the major mechanism of action.[17,22,25] Interestingly, these molecules were found to bind in the heparin-binding site of these enzymes and induce allosteric inhibition.[22,25]

Sulfated LMW lignins are similar to unfractionated heparin (UFH) or LMW heparins in terms of structural polydispersity and heterogeneity (FIG. 1). The molecules are composed of oligomeric chains of varying lengths, which can be 5-15 units long, and inter-monomeric linkages, which include β-O4, β-5, β-β, 5-5 and others.[24] Theoretically, more than 36,000 hexameric sequences are possible from these variations. Yet, sulfated LMW lignins are completely unlike heparins with regard to their backbone. In contrast to the polysaccharide backbone of the heparins, sulfated LMW lignins possess a highly aromatic scaffold. In fact in terms of structure, sulfated LMW lignins are unlike any other class of anticoagulant investigated to-date, including the heparins, the coumarins, the hirudins, the peptidomimetics and the small molecule direct inhibitors.

In this Example, we report on the development of a sulfated β-O4 lignin (SbO4L), a chemically synthesized lignin, which exhibits highly selective and potent inhibition of human thrombin (and plasmin). SbO4L is homogeneous with regard to its inter-monomer linkages. It inhibits thrombin through an allosteric process by binding in exosite 2. Human whole blood studies demonstrate that SbO4L-based anticoagulation that is comparable to that induced by enoxaparin. Most importantly, SbO4L is synthesized in a few simple steps from readily available small molecules, which bodes well for a relatively inexpensive alternative to UFH and LMW heparin. Additionally, SbO4L inhibition of thrombin is quantitatively and rapidly reversed by protamine, which should greatly increases confidence in its usage. Thus, this Example describes a family of completely synthetic, non-polysaccharide, non-animal derived, thrombin-selective, allosteric anticoagulants which may be used in treating human and animal subjects.

Experimental Procedures

Proteins and Chemicals.

Human proteases were from either Haematologic Technologies (Essex Junction, Vt.), Sigma-Aldrich (St. Louis, Mo.), or Elastin Products Company (Owensville, Mo.). Chromogenic substrates were obtained either from Sekisui Diagnostics (Stamford, Conn.), Sigma-Aldrich or Diapharma (West Chester, Ohio). HirP, a Tyr63-sulfated hirudin-(54-65) peptide labeled with 5-(carboxy)fluorescein, i.e., [5F]-Hir[54-65]($SO_3^-$), was from the Bock laboratory.[26] Monomer used in SbO4L preparation was synthesized using literature protocol.[27] Plasma and whole blood clotting reagents were from Fisher Diagnostics (Middletown, Va.) or Haemoscope Corporation (Niles, Ill.).

Chemical Synthesis of Sulfated β-O4 Lignin (SbO4L).

The synthesis of SbO4L was developed from reported polymerization and sulfation strategies. Briefly, $K_2CO_3$ and ethyl 2-bromo-3-(4-hydroxy-3-methoxyphenyl)-3-oxo-propanoate were stirred in anhydrous DMF under nitrogen for 24 h, poured into ice-water mixture and the pH adjusted to ~2.5 with 2M HCl. The precipitated polymer was filtered and lyophilized. The solid was suspended in methanol at 50° C. and $NaBH_4$ carefully added. After 24 h, the solution was neutralized with acetic acid, poured into 0.5M HCl and precipitated polymer was isolated by centrifugation. The solid was then dissolved in 1,4-dioxane and high molecular weight chains precipitated in diethyl ether. The reduced polymer was sulfated with triethylamine-sulfur trioxide complex in anhydrous DMF at 65° C. for 24 h,[30,31] dissolved in 30% (w/v) aqueous sodium acetate and poured into ice-cold ethanol to precipitate crude SbO4L. The recovered solid was desalted using FloatALyzer G2 (Spectrum Labs) dialysis tubes (MWCO 0.1-0.5 kDa) and lyophilized.

Molecular Weights of SbO4L.

The number—($M_N$), weight—($M_W$), and peak—($M_P$) average molecular weights of SbO4L were measured as described earlier.[23] Briefly, gel permeation chromatography (GPC) of SbO4L was performed on a Phenogel 5μ column (Phenomenex, Torrance, Calif.) using 0.1 N NaOH mobile phase flowing at 0.7 ml/min with detection at 254 nm. The SbO4L chromatogram was sliced into 1000 time periods providing 1000 average molecular weights with their corresponding absorbances, which were used to calculate $M_W$, $M_N$, and $M_P$ values.[23]

Direct Inhibition of Proteases.

Inhibition of coagulation enzymes (thrombin, factors Xa, IXa, XIa and VIIa) by SbO4L was measured using chromogenic substrate hydrolysis assays in standard manual 1 ml cuvettes, as described previously,[17,21,22,25] while inhibition of other proteases was measured using a 96-well microplate format. This protocol was also adopted for studying thrombin inhibition in the presence of antithrombin or in the presence of serum albumin. The buffers, conditions and chromogenic substrates used in these experiments were derived from the literature. Briefly, a SbO4L in an appropriate buffer was incubated with a target protease for 10 min, followed by addition of chromogenic substrate and rapid measurement of the initial rate of substrate hydrolysis ($A_{405}$). The ratio of the initial rate in the presence and absence of SbO4L gave the residual protease activity at each inhibitor concentration from which the $IC_{50}$ was calculated using logistic equation 1.

$$Y = Y_0 + \frac{Y_M - Y_0}{1 + 10^{\{\log[SbO4L]_0 - \log IC_{50}\} \times HS}} \qquad \text{Eq. 1}$$

In this equation, Y is the residual protease activity; $Y_M$ and $Y_0$ are the maximum and minimum residual activities, respectively; $IC_{50}$ is the concentration of the inhibitor that results in 50% inhibition of enzyme activity; and HS is the Hill slope.

Inhibition of Thrombin-Thrombomodulin-Mediated Activation of Protein C by SbO4L.

The protocol for measuring the activation of protein C by thrombin-rTM complex essentially followed the literature.[32] Briefly, 5 μl of SbO4L (2.3 ng/ml to 2.3 mg/ml) was added to 70 μl of 50 mM Tris-HCl buffer, pH 7.4, containing 100 mM NaCl, and 1 mM $CaCl_2$ at 37° C., followed by addition of 5 μl of thrombin (240 nM) and 5 μl of rTM (400 nM). To this mixture, 5 μl of protein C (10 μM) was added followed by incubation for another 10 min. At the end of this period, APC generation was quenched with 5 μl of 10 mM EDTA and 16 μM argatroban, and quantified from the initial rate of hydrolysis of 400 μM S-2366. The apparent $IC_{50}$ of SbO4L inhibition of activation of protein C was calculated using equation 1.

Michaelis-Menten Kinetics and Competitive Binding Studies.

The kinetics of substrate hydrolysis by thrombin in the presence of SbO4L and competitive studies with exosite 1 and exosite 2 ligands followed our protocols for sulfated LMW lignins.[17-19,22]

Plasma and Whole Blood Clotting Assays.

The protocol for human plasma activated partial thromboplastin (APTT) and prothrombin time (PT), and human whole blood thromboelastography (TEG) and hemostasis analysis (HAS) in the presence and absence of SbO4L followed our earlier studies with sulfated LMW lignins.[18,19,21,23]

Reversal of SbO4L Activity by Protamine.

Protamine (4.9 μg/l to 14.8 g/l was added to a solution of SbO4L-thrombin complex in a 20 mM Tris-HCl buffer, pH 7.4, containing 100 mM NaCl, 2.5 mM $CaCl_2$ and 0.1% PEG8000 at 37° C. followed by measuring the residual thrombin activity from substrate hydrolysis, as described above. In the absence of protamine, SbO4L gave ~50% inhibition of thrombin at 37° C. Protamine alone did not affect the activity of thrombin as assessed by appropriate controls.

Results

Synthesis and Characterization of SbO4L.

Of the several inter-residue linkages present in lignins, the β-5 and β-O4 linkages are most abundant.[33] Earlier work had shown that sulfated LMW lignins devoid of the β-5 linkage, and hence enriched in β-O4 linkage, generated significant anticoagulant activity.[22,23] Based on this, we reasoned that a lignin containing only β-O4 linkage may exhibit much higher anticoagulation potential. Hence, we resorted to a wholly chemical process of alkaline polymerization of ethyl 2-bromo-3-(4-hydroxy-3-methoxyphenyl)-3-oxo-propanoate followed by sodium borohydride reduction and sulfation using triethylamine-sulfur trioxide complex (FIG. 1). Each of these steps have been reported earlier for a variety of other reactants and were achieved in fairly high yields.[28-31]

SbO4L is a Selective, Direct Inhibitor of Human Thrombin.

Figure 2:
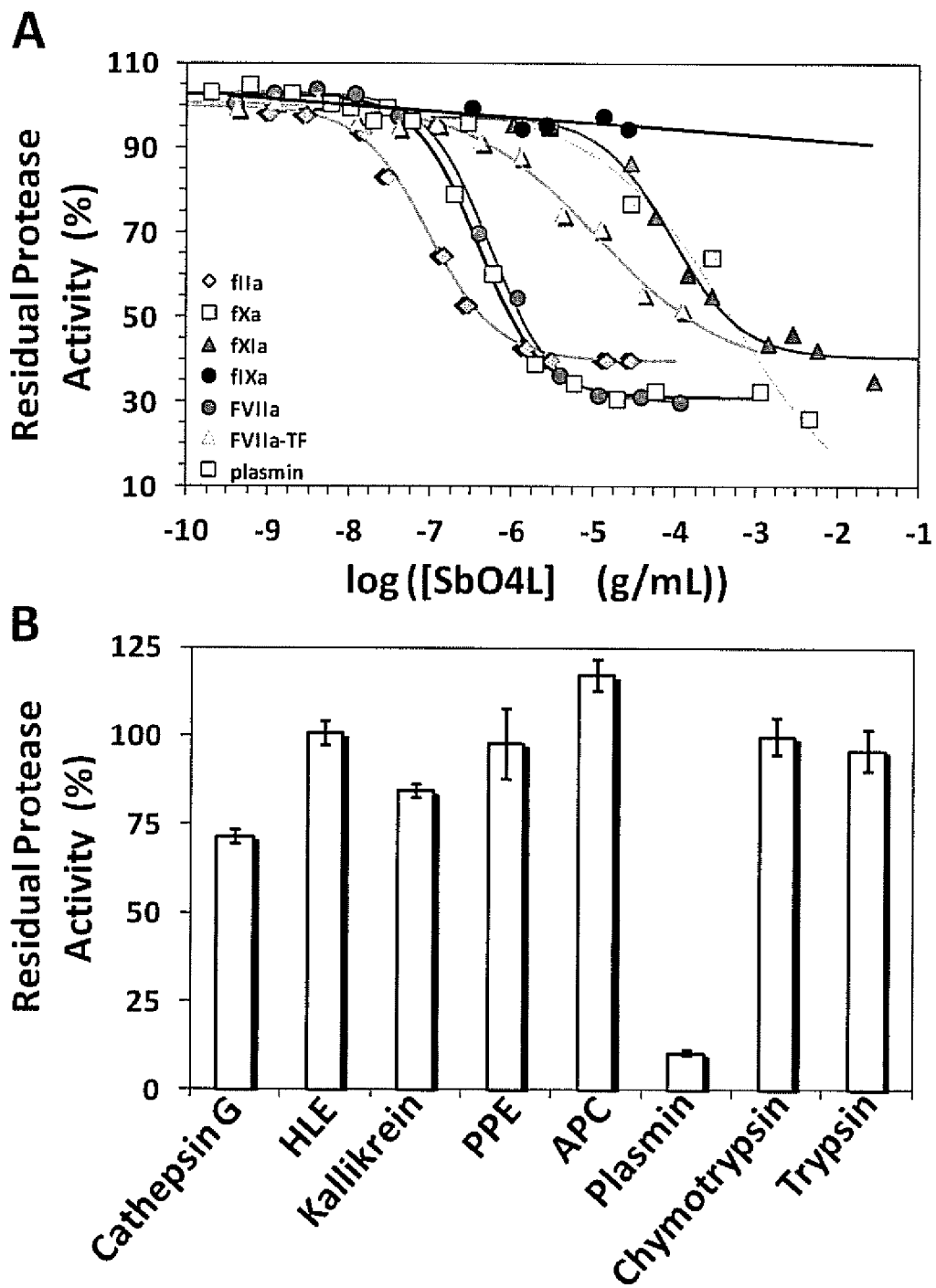
FIG. 2 Direct inhibition of serine proteases by SbO4L. A) The inhibition of factors IIa (thrombin), Xa, XIa, IXa and VIIa, VIIa-tissue factor (TF) complex, and plasmin by SbO4L was studied using chromogenic substrate hydrolysis assay. Solid lines represent sigmoidal dose-response fits (Eq. 1) to the data to obtain $IC_{50}$. B) SbO4L inhibition of other heparin-binding serine proteases including cathepsin G, human leukocyte elastase (HLE), porcine pancreatic elastase (PPE), activated protein C (APC), plasmin, chymotrypsin and trypsin at a fixed 373 µg/l (~1800-fold excess over the $IC_{50}$ of thrombin inhibition). Error bars were derived from non-linear regression and represent ±1 S.E.

The inhibition of coagulation factors IIa, Xa, IXa, XIa and VIIa was studied using spectrophotometric measurement of the residual protease activity in the presence of varying levels of SbO4L. FIG. 2A shows the decrease in residual protease activity as the concentration of SbO4L was varied over ~$10^5$-fold. Previous studies have shown that UFH, LMW heparin and fondaparinux do not inhibit these enzymes at concentrations as high as 100 µg/ml.[22] The change in activity was fitted using the dose-response equation 1 to calculate $IC_{50}$ (Table 1).

TABLE 1

Parameters for sulfated β-O4 lignin (SbO4L) inhibition of coagulation proteases.[a]

| Protease | log {$IC_{50}$ (g/ml)} | $IC_{50}$ (µg/ml) | $Y_M$ | $Y_0$ | HS |
|---|---|---|---|---|---|
| Thrombin | −6.8 ± 0.1[b] | 0.17 ± 0.01 | 99 ± 1 | 29 ± 1 | 1.6 ± 0.1 |
| Factor Xa | −3.3 ± 0.6 | 500 ± 300 | 100 ± 4 | ~1 | 0.5 ± 0.2 |
| Factor IXa | NI[c] | NI | —[d] | — | — |
| Factor XIa | −4.1 ± 0.1 | 89 ± 9 | 98 ± 3 | 41 ± 2 | 1.0 ± 0.2 |
| Factor VIIa | −6.3 ± 0.1 | 0.54 ± 0.05 | 103 ± 3 | 31 ± 3 | 1.1 ± 0.1 |
| Factor VIIa - TF | ~−5.0[e] | >11[e] | 100 ± 2 | ~38[e] | ~0.5[e] |
| Plasmin | −6.4 ± 0.1 | 0.38 ± 0.04 | 103 ± 1 | 31 ± 2 | 1.1 ± 0.1 |
| Thrombin w/AT[f] | −6.7 ± 0.1[b] | 0.20 ± 0.01 | 64 ± 1 | 6 ± 1 | 1.9 ± 0.4 |
| Thrombin/rTM - PC[g] | −5.4 ± 0.1 | 4.20 ± 0.08 | 98 ± 2 | 3 ± 5 | 0.96 ± 0.14 |

[a]The $IC_{50}$, HS, $Y_M$, $Y_O$ values were obtained following non-linear regression analysis of direct inhibition of the protease (see 'Experimental Methods' for details).
[b]Errors represent ±1 S.E.
[c]No inhibition was observed upto concentrations as high as 1 mg/ml.
[d]Not applicable.
[e]Estimated values.
[f]In the presence of 200 nM AT.
[g]Inhibition of activation of protein C by thrombin - thrombomodulin complex.

The $M_N$, $M_W$ and $M_P$ of SbO4L were measured using aqueous GPC-HPLC, as described earlier,[23] and found to be 9200, 12300, and 9100, respectively. This implies that on an average SbO4L oligomer is nearly 23 residues long. In comparison, an average full-length heparin chain is ~50 saccharides in length, whereas an average LMW heparin chain has 16 residues. The GPC-HPLC chromatograms also indicated absence of species with molecular weight less than 1000 suggesting an enriched preparation of longer oligomers that constituted composition greater than 95%. The polydispersity, i.e., the ratio of $M_W$ to $M_N$, of SbO4L was found to be 1.336, which is similar to that of UFH used in the clinic. The sulfation density calculated on the basis of the difference in $M_W$ between SbO4L and its unsulfated precursor was ~2 sulfate groups per monomer. Elemental analysis measurements indicated a composition of C, 35.39; H, 4.15; and S, 11.54; which match a hypothetical SbO4L chain of 23 residues containing 27 sulfate groups and calculated composition of C, 35.20; H, 4.02; S, 11.08. This indicates an average of 1.2 sulfate groups per monomer. These measurements compare favorably with that of UFH and LMW heparins, which show an average of ~1.6 anionic groups per monomer. Additional purity and consistency of SbO4L preparation studies were performed using reversed-phase ion pairing UPLC-MS, and in vitro thrombin inhibition tests on three independent batches of synthetic SbO4L. The three batches demonstrated essentially identical UPLC-MS fingerprints and indistinguishable $IC_{50}$ for thrombin inhibition. Thus overall, the elemental analysis measurements in combination with UPLC-MS fingerprints indicate the presence of uniform β-O4 linkage in SbO4L preparation in high purity (>95%) in comparison to sulfated LMW lignins studied earlier.

SbO4L inhibits thrombin with an $IC_{50}$ of 0.17 µg/ml, which corresponds to ~14 nM (Table 1). Intrinsic pathway proteases factors Xa and XIa were also inhibited by SbO4L, however the $IC_{50}$ values were in the range of 90-500 µg/ml corresponding to 10-55 µM. With regard to factor IXa, essentially no inhibition was noticeable at concentrations as high as 28.7 µg/ml (FIG. 2A). Thus, SbO4L inhibited thrombin nearly 590-2940-fold better than these coagulation enzymes.

With regard to the extrinsic pathway, SbO4L was found to inhibit factor VIIa with an $IC_{50}$ of 0.54 µg/ml (FIG. 2A, Table 1), only 3-fold higher than that for thrombin. Yet, in the presence of recombinant tissue factor (rTF), the potency decreased by more than 55-fold. Factor VIIa-rTF complex is the more relevant physiologic protease and this suggests that SbO4L is likely to primarily target the propagation step of coagulation.

To assess the selectivity features of SbO4L in more detail, we studied a small group of heparin-binding serine proteases including cathepsin G, HLE, kallikrein, PPE, APC, plasmin, chymotrypsin, and trypsin. The inhibition of these proteases by sulfated LMW lignins, parent molecules from which SbO4L was designed, was studied earlier.[25] The activity of each protease was measured in a spectrophotometric assay in the presence of SbO4L at 0.37 (FIG. 2B) and 1.62 mg/ml, which represent ~1850- and 8100-fold higher concentrations than the $IC_{50}$ of thrombin inhibition. Except for human plasmin, none of the other proteases studied were found to be appreciably inhibited by SbO4L. For plasmin, a dose-response study led to an $IC_{50}$ of 0.38 µg/ml (FIG. 2A, Table 1) suggesting potency similar to that against thrombin. In toto, results indicate that SbO4L is a selective inhibitor of human thrombin and plasmin, despite the considerable structural similarity between these trypsin-like proteases. Such high selectivity has not been observed earlier.[22,25]

SbO4L Inhibition of Thrombin is Unaffected by the Presence of Antithrombin.

Polymeric heparin is a powerful antagonist of thrombin because of its ability to bind plasma antithrombin and bridge with thrombin.[1,34] In contrast, sulfated LMW lignins were found to bind the serpin with reasonable affinity, yet loose direct inhibition potential.[24] To assess the influence of antithrombin on SbO4L activity, direct inhibition of thrombin was studied in the presence of 200 nM serpin under otherwise identical conditions. A decrease in thrombin activity with increasing SbO4L levels was observed, which was identical to that measured in the absence of the serpin, except for the differences in maximal ($Y_M$) and minimal ($Y_O$) residual thrombin activities. The $Y_M$ and $Y_O$ values decreased by 35% and 23%, respectively, due to the reaction of thrombin with antithrombin. However these changes did not affect SbO4L inhibition of thrombin ($IC_{50}$=0.2 and 0.17 µg/ml with and without antithrombin, respectively (Table 1)). From this result it can be inferred that antithrombin does not retard or stimulate SbO4L's inhibitory activity. This is a significant point of variance from the parent sulfated LMW lignins, for which the serpin-mediated pathway was found to be a competing side reaction.[24] The results highlight an interesting structural aspect that a specific scaffold, i.e., the β-O4-linked scaffold, of the many possible in sulfated LMW lignins does not appear to bind the serpin with high affinity, which improves mechanistic selectivity.

SbO4L Inhibits Activation of Protein C by Thrombin-rTM Complex.

Figure 3:
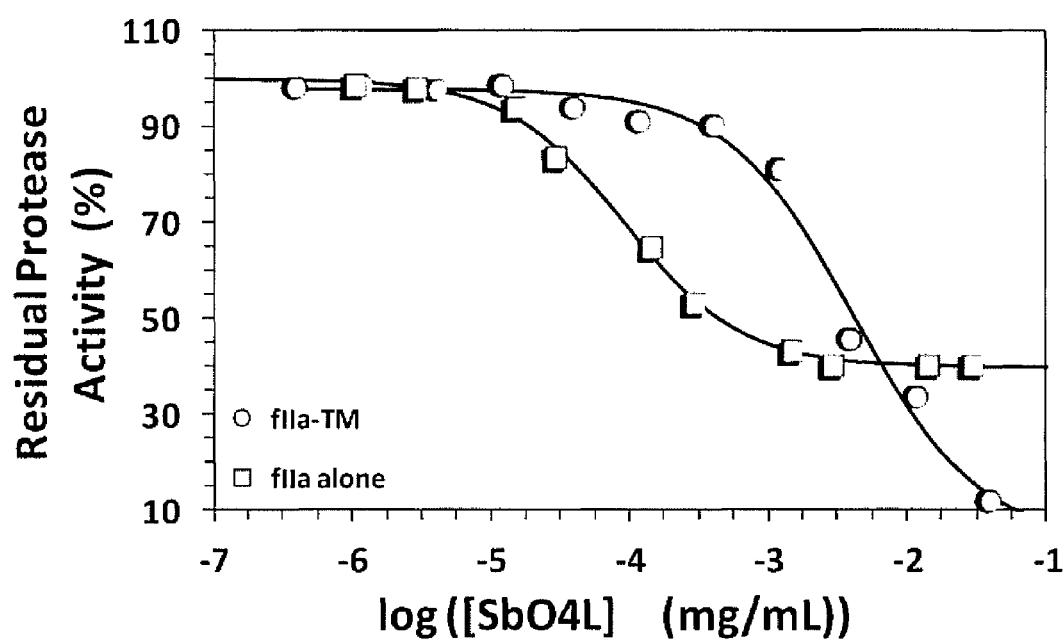
FIG. 3 SbO4L Inhibition of thrombin-thrombomodulin activation of protein C. Formation of APC (o) in the presence of SbO4L was followed using S-2366 hydrolysis by thrombin-TM complex under standard assay conditions after neutralization of thrombin activity using argatroban (see Experimental for details). For comparison, SbO4L inhibition of thrombin's proteolytic activity is also shown (∉). Solid lines represent sigmoidal dose-response fits (Eq. 1) to the data to obtain $IC_{50}$.

Thrombin's procoagulant activity is drastically modulated by cell surface TM, which transforms it into an anticoagulant protease with specificity for protein C.[35,36] To assess whether TM binding to thrombin alters the activity of SbO4L, we studied the efficacy of protein C activation. The level of proteolytically active protein C formed by thrombin-rTM complex can be measured spectrometrically through hydrolysis of S-2366[32] following suppression of thrombin's native proteolytic activity using argatroban (~100×$K_1$)[37] as its specific inhibitor. Measurement of APC levels in the presence of varying SbO4L levels led to a sigmoidal profile on a semi-log plot (FIG. 3) suggesting that as the SbO4L inhibited the protein C activation potential of thrombin-rTM complex. The $IC_{50}$ was measured to be 4.2 µg/ml (Table 1), which was ~20-fold higher than that measured for SbO4L inhibiting the procoagulant activity of thrombin alone. Interestingly, the efficacy of inhibition of protein C activation was found to be nearly 100% (Table 1), which is significantly higher than that for thrombin alone (~60%, Table 1). The results indicate that SbO4L reduces the procoagulant potential of thrombin much more than the anticoagulant potential.

SbO4L is an Allosteric Inhibitor of Thrombin.

Figure 4:
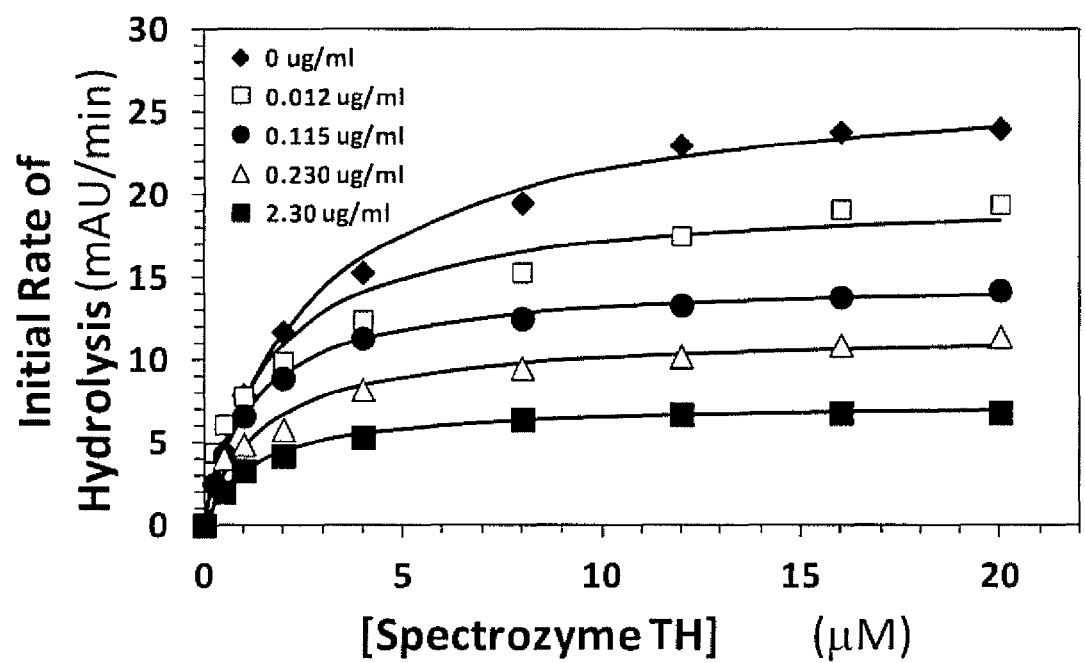
FIG. 4 Michaelis-Menten kinetics of Spectrozyme TH hydrolysis by thrombin in the presence of SbO4L. The initial rate of hydrolysis at various substrate concentrations was measured in a pH 7.4 buffer (50 mM Tris-HCl buffer, pH 7.4, containing 100 mM NaCl, and 1 mM $CaCl_2$ at 37° C.). The concentrations of SbO4L were 0 (♦), 0.012 (∉), 0.115 (●), 0.230 (Δ) and 2.3 µg/ml (■). Solid lines represent non-linear fits to the data using the standard Michaelis-Menten equation.

To understand the basis of thrombin inhibition, we measured the kinetics of Spectrozyme TH hydrolysis at pH 7.4 in the presence for SbO4L. Plots of the initial rates versus substrate concentration were hyperbolic, as expected (FIG. 4). As the concentration of SbO4L was increased from 1.2 ng/ml to 2.3 µg/ml, maximal velocity of hydrolysis, $V_{MAX}$, decreased steadily. Fitting the data using the standard Michaelis-Menten equation gave an essentially invariant $K_{M,app}$ of 1.5 µM. This suggests that SbO4L does not affect small molecule chromogenic substrate binding to the active site of thrombin. The $V_{MAX}$ decreased from 27.5 to 7.4 mAbsU/min (FIG. 4) corresponding to a decrease of more than 70%. Thus, SbO4L appears to not sterically hinder the interaction of thrombin substrate, but brings about changes in the active site that reduce the catalytic rate. This implies that SbO4L is a non-competitive, allosteric inhibitor of human thrombin.

Allostery Arises from Binding in Exosite 2 of Thrombin and not in Exosite 1.

Figure 5:
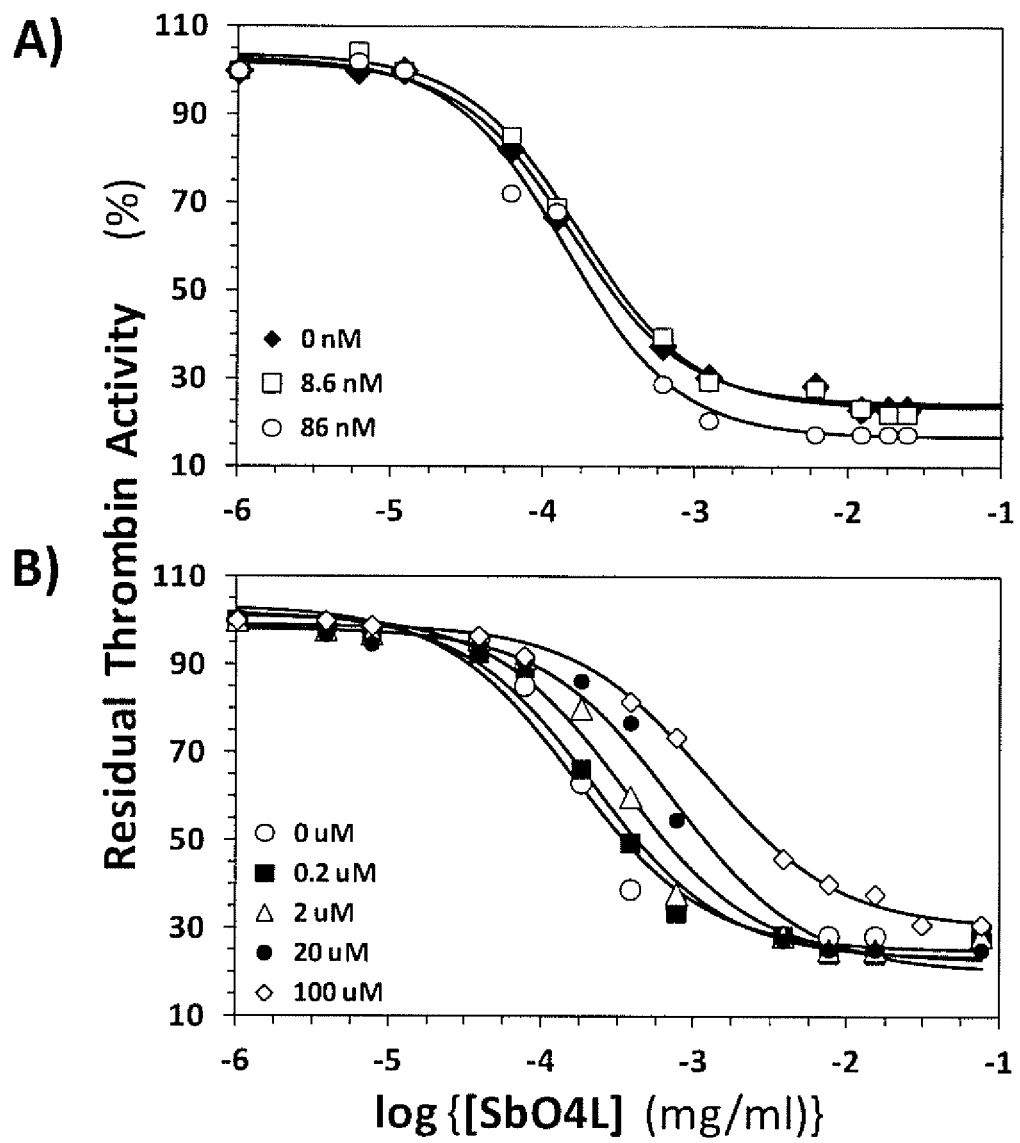
FIG. 5 Competitive effect of a hirudin peptide HirP (A) and UFH (B) on the direct inhibition of thrombin by SbO4L. Thrombin inhibition by SbO4L in the presence of a constant concentration of HirP (A) or UFH (B) was measured through the Spectrozyme TH hydrolysis assay at pH 7.4. Solid lines represent fits by the dose-response equation to obtain the apparent $IC_{50}$ (50 mM Tris-HCl buffer, pH 7.4, containing 100 mM NaCl, and 1 mM $CaCl_2$ at 37° C.). The concentrations of HirP chosen for study include 0 (♦), 8.6 (□), and 86 nM (○), while that of UFH were 0 (○), 0.2 (■), 2 (Δ), 20 (●) and 100 µM (◇).

To decipher the origin of allostery, we measured the effect of HirP, a hirudin-based dodecapeptide, on the SbO4L inhibition of thrombin. Earlier work has shown that HirP binds in exosite 1 with an affinity of 28 nM and increases the catalytic efficiency of thrombin.[26] Thus, thrombin inhibition by SbO4L was studied in the presence of the exosite 1 competitor (FIG. 5A). As the concentration of the dodecapeptide was increased from 0 to 3.1-times its affinity, the apparent $IC_{50}$ of thrombin inhibition remained essentially invariant at 0.15 µg/ml (Table 2).

TABLE 2

Inhibition of human thrombin by SbO4L in the presence of HirP, an exosite 1 ligand, and UFH, an exosite 2 ligand, at pH 7.4 and 25° C.[a]

|  | $IC_{50}$ (µg/ml) | $Y_m$ | $Y_0$ | HS |
|---|---|---|---|---|
| [HirP] nM |  |  |  |  |
| 0 | 0.15 ± 0.01[b] | 102 ± 14 | 24 ± 1 | 1.2 ± 0.1 |
| 8.6 | 0.17 ± 0.02 | 103 ± 2 | 23 ± 1 | 1.2 ± 0.1 |
| 86 | 0.14 ± 0.02 | 102 ± 3 | 17 ± 2 | 1.2 ± 0.2 |
| [UFH] µM |  |  |  |  |
| 0.2 | 0.22 ± 0.01 | 99 ± 1 | 26 ± 1 | 1.6 ± 0.1 |
| 2.0 | 0.34 ± 0.02 | 98 ± 1 | 26 ± 1 | 1.8 ± 0.1 |
| 20 | 0.66 ± 0.05 | 96 ± 1 | 24 ± 1 | 1.6 ± 0.2 |
| 100 | 1.25 ± 0.14 | 100 ± 1 | 28 ± 2 | 0.9 ± 0.1 |

[a]The $IC_{50}$, HS, $Y_M$, $Y_O$ values were obtained following non-linear regression analysis of direct inhibition of human thrombin in 20 mM Tris-HCl buffer, pH 7.4, containing 100 mM NaCl, 2.5 mM CaCl$_2$, and 0.1% polyethylene glycol (PEG) 8000 at 25° C. Inhibition was monitored through spectrophotometric measurement of residual thrombin activity.
[b]Errors represent ±1 S.E.

These results imply that the interaction of HirP with thrombin does not affect SbO4L inhibition to a significant extent suggesting that the allosteric inhibitor does not engage exosite 1.

To assess whether SbO4L binds in exosite 2 of thrombin, we studied competition with UFH. FIG. 5B shows the change in the dose-response profiles of SbO4L inhibiting thrombin in the presence of UFH at pH 7.4. As the concentration of UFH increased from 0.2 to 100 µM, the $IC_{50}$ increased from 0.22 to 1.25 µg/ml (Table 2) indicating that SbO4L competes with UFH for binding to human thrombin.

The efficacy of competition can be gauged by using the Dixon-Webb relationship (Eq. 2), which estimates the ideality of competition between two ligands. In this equation, $K_{UFH}$ is the dissociation constant of thrombin-UFH complex, which was measured to be 15.6±3.1 µM under otherwise identical conditions. Analysis using equation 2 showed that the observed $IC_{50}$ was equivalent to that predicted on the basis of ideal competition. For example at 100 µM UFH, the predicted $IC_{50}$ is 1.1 µg/ml, while the observed $IC_{50}$ was 1.25 µg/ml. Thus, SbO4L binds in or near anion-binding exosite 2.

$$IC_{50,predicted} = IC_{50}\left(1 + \frac{[UFH]_O}{K_{UFH}}\right) \quad \text{Eq. 2}$$

SbO4L is a Potent Anticoagulant in Human Plasma.

Figure 6:
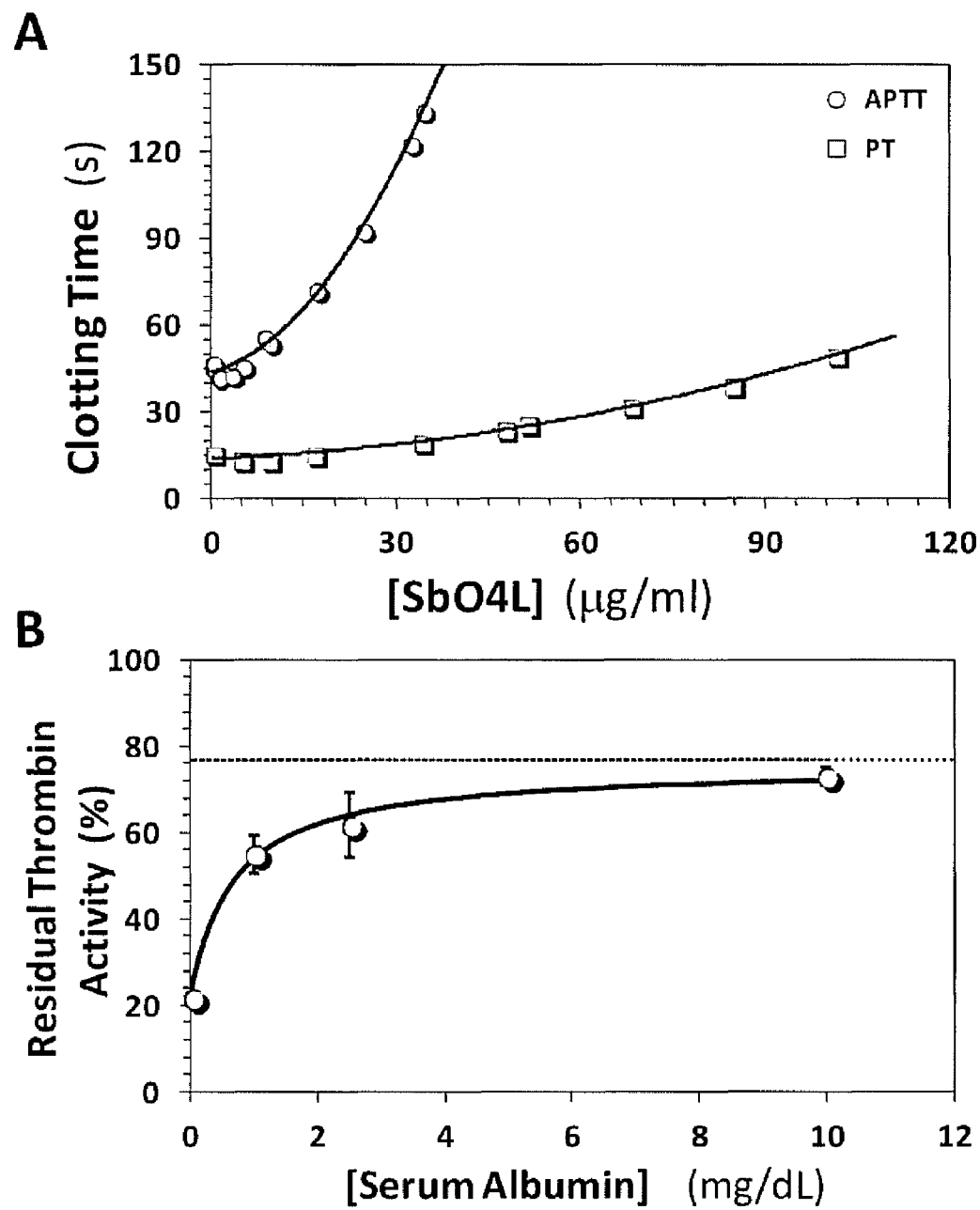
FIG. 6. Effect of SbO4L in human plasma. A) Prolongation of clotting time as a function of SbO4L concentration in either the prothrombin time (PT) or the activated partial thromboplastin time (APTT) assay. The solid lines are trend lines, and not exponential fits. Errors in clotting time measurement were in the range of symbol size and have been omitted. B) Effect of serum albumin on the anticoagulant potential of SbO4L. Solid line to the data represents a rectangular hyperbolic fit to the data to derive the maximal thrombin activity at limiting concentrations of BSA. The dotted line represents the maximal thrombin activity.

Prothrombin (PT) and activated partial thromboplastin times (APTT) are traditional measures of the anticoagulation state of human plasma. FIG. 6A shows the variation in plasma PT and APTT in the presence of SbO4L. A significant concentration-dependent prolongation of clotting times was observed suggesting good anticoagulation potential. A 2-fold increase in PT required 68 µg/ml, corresponding to 7.5 µM, which is significantly lower than that needed for a generic LMW heparin (142 g/ml, 31.6 µM) and a clinically used LMW heparin (enoxaparin, 339 µg/ml or 75 µM).[21] Likewise, a two-fold increase in APTT required 20 µg/ml (2.2 µM) of SbO4L, which compares favorably with a concentration of 5.9 µg/ml (1.3 µM) for generic LMW heparin and 5.4 µg/ml (1.2 µM) for enoxaparin.[21] These results show that SbO4L is nearly as potent as LMW heparins in inducing plasma anticoagulation.

Despite this high potency (comparable to enoxaparin), SbO4L displays a loss of ~100-340-fold in potency in human plasma from that in in vitro enzyme systems. To assess the basis for this difference, we studied the effect of serum albumin on the effectiveness of SbO4L. FIG. 6B shows the change in relative thrombin activity in the presence of fixed concentration of SbO4L and varying concentrations of bovine serum albumin (BSA), a surrogate for its human counterpart. In the absence of BSA, thrombin's hydrolytic activity was 22% ([SbO4L]=0.42 µg/ml), which was found to increase to 56, 59 and 72% in the presence of 1, 2.5 and 10 mg/dl BSA, respectively. This suggests that the presence of BSA results in a significant drop in inhibitor potency probably arising from non-specific sequestering of SbO4L. Interestingly, a maximal thrombin activity of ~75% is reached suggesting that some SbO4L remains free, and therefore inhibitory, at high enough plasma albumin concentration.

SbO4L is a Potent Anticoagulant of Human Whole Blood as Measured by Thromboelastography (TEG®).

To evaluate SbO4L as an anticoagulant in whole blood, we employed TEG®, which is quite often used to monitor anticoagulation therapy with LMW heparins.[21] TEG® assesses the nature of physical forces within a clot, which are dramatically affected by the presence of an anticoagulant in blood. In a nutshell, the clot formation in TEG® is recorded as a force transduced on a pin at the center of a blood-containing cup. Several parameters are evaluated from this force measurement including maximum amplitude (MA), the shear elastic modulus (G), the reaction time (R) and the angle α. MA and G are measures of clot stiffness, while R and α are measures of the rate of clotting.

FIG. 9 shows the change in R, α, MA and G parameters as a function of the concentration of SbO4L. Briefly, as the concentration of SbO4L increases from 0 to 152 µg/ml, R increases from 7.7 to 25.9 min, while α decreases from 56° for normal blood to 22° indicating that the kinetics of fibrin polymerization and network formation is significantly depressed by the presence of SbO4L. Enoxaparin behaves in a similar manner, except that its effective concentrations range from 1-5 µg/ml. Likewise, SbO4L reduces MA and G in a manner similar to enoxaparin (FIG. 9), except for the ~30-fold better potency of the latter (~15-fold molar basis).

Whole Blood Anticoagulation Potency of SbO4L by Hemostasis Analysis (HAS™).

Figure 7:
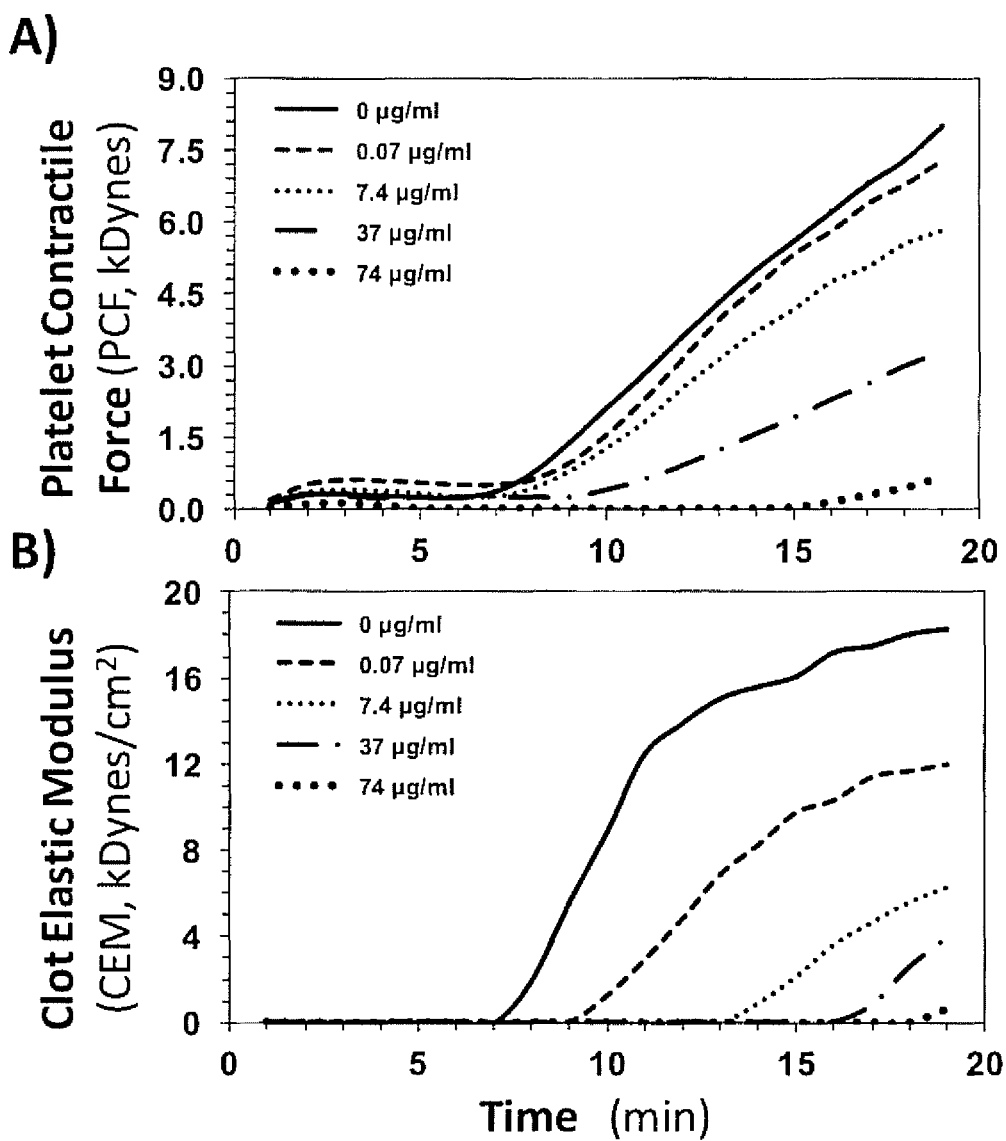
FIG. 7. Comparison of the effect of SbO4L on platelet function in whole blood using hemostasis analysis system (HAS™). A) and B) show the change in platelet contractile force (PCF) and clot elastic modulus (CEM), respectively, with time at various fixed concentrations of SbO4L (0-74 µg/ml).

To further assess the whole blood anticoagulant potential of SbO4L, we utilized HAS™, which evaluates platelet contribution to clot formation (FIG. 7).[21] This technique evaluates clot structure through the measurement of clot elastic modulus (CEM), which is the ratio of stress induced by platelets to strain arising from the change in clot thickness. The technique also provides information on contractile forces between platelets, i.e., the platelet contractile force (PCF), that adhere to surfaces and restrict relative movement of two cups. PCF depends on the platelet number, their metabolic status, presence of thrombin inhibitors and degree of GPIIb/IIIa exposure.[38] On the other hand, CEM depends on the clot micro-structure, fibrinogen concentration, and thrombin formation rate. It has been suggested that PCF and CEM changes can be correlated with susceptibility to bleeding and/or thrombotic tendency.

SbO4L affects PCF and CEM in a dose-dependent manner (FIG. 9). As the concentration of SbO4L increases from 0 to 74 µg/ml, the PCF and CEM decrease from 8.0 to 0.7 kDynes and 18.3 to 0.6 kDynes/cm², respectively. These results parallel those measured through TEG®. When comparisons are made with enoxaparin, strikingly similar results are observed except for the range of concentration used for the clinically used anticoagulant. Whereas PCF value of 0.7 was achieved at 74 µg/ml (8.1 µM) for SbO4L, it was achieved at 2.0 µg/ml (444 nM) for enoxaparin suggesting a ~37-fold better potency for the latter on weight basis and 18-fold better potency on molar basis. These results further confirm that SbO4L mimics enoxaparin anticoagulation function fairly well.

SbO4L Anticoagulation can be Reversed by Protamine.

Figure 8:
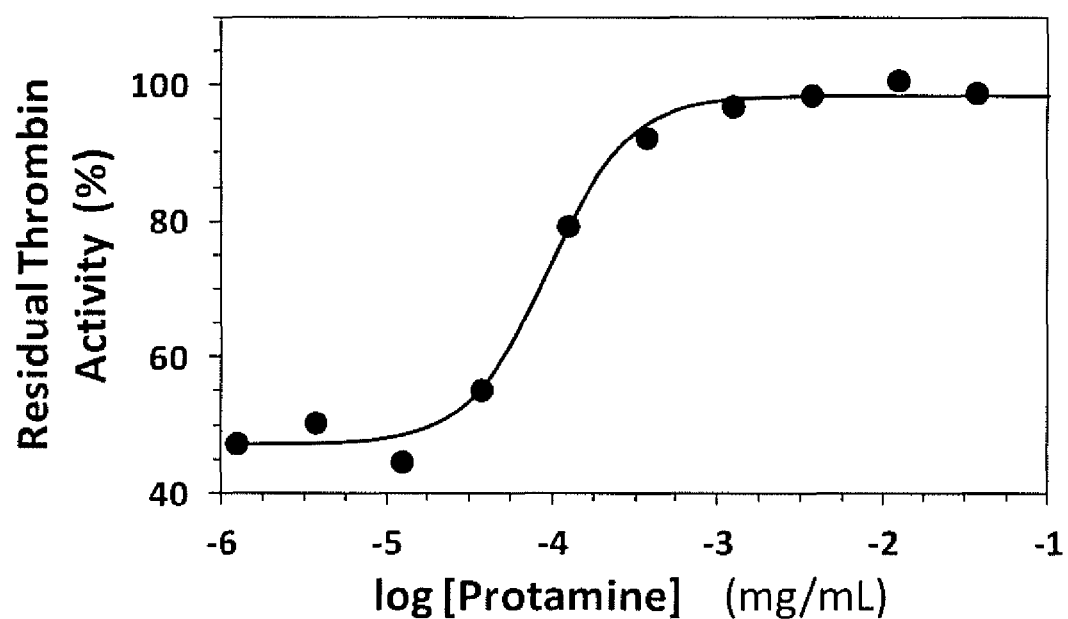
FIG. 8. Protamine-mediated reversal of SbO4L inhibition of thrombin. Recovery of thrombin activity at varying levels of protamine following 50% inhibition by SbO4L was measured through the Spectrozyme TH hydrolysis assay at pH 7.4. Solid line represents non-linear fit of the data by a logistic function similar to equation 1 to obtain the $RC_{50}$, the concentration of protamine necessary to recover 50% thrombin activity.

A major advantage of heparin therapy is its amenability to protamine-based reversal. It is also one of the reasons why fondaparinux continues to suffer because its iatrogenic bleeding is difficult to reverse rapidly. To test whether SbO4L inhibition of thrombin can be reversed, we studied the recovery of thrombin activity following successive introduction of protamine. FIG. 8 shows the thrombin recovery profile with varying levels of protamine after achieving 50% inhibition with SbO4L. The protamine-mediated recovery profile essentially mirrors the SbO4L-induced inhibition profile. More importantly, the level of recovery is quantitative at high enough protamine concentrations. Further, the recovery was instantaneous as no extended incubation was necessary to observe reversal. The concentration of protamine necessary to recover 50% thrombin activity, i.e., $RC_{50}$, could be calculated using an equation similar to the logistic equation 1 used for inhibition studies and found to be ~0.1 µg/ml, a concentration equivalent to the $IC_{50}$ for SbO4L inhibition of thrombin.

In Vivo Assays.

Two mouse models were used to analyze the anticoagulant potential of SbO4L.

$FeCl_3$ Carotid Artery Thrombosis Model.

The ferric chloride induced injury model is commonly used to analyze the anticoagulant potential of several compounds in mice. Wild type C57B1/6 mice were anesthetized with 50 mg/kg intraperitoneal (IP) pentobarbital. SbO4L (0, 100, 300, 500 or 1000 µg in 100µ phosphate buffered saline (PBS)) was infused into the right internal jugular vein. Five minutes after infusion the right common carotid artery was exposed and fitted with a Doppler flow probe. Thrombus formation was induced by applying two 1×1.5 mm filter papers saturated with $FeCl_3$ (3.5% solution) to opposite sides of the artery for three minutes. After washing the site of injury with PBS, flow was monitored for thirty minutes. Mice were sacrificed by pentobarbital overdose after conclusion of the experiment while under anesthesia.

Rose Bengal-Laser Injury Carotid Artery Thrombosis Model.

In vivo testing using Rose Bengal thrombosis model is another recognized mouse model used to perform anticoagulant assays. Mice were anesthetized as discussed above and 500 µg of SBO4L in 100 µl PBS was infused into the right internal jugular vein. Five minutes after infusion, Rose Bengal (75 mg/kg) was infused through the internal jugular vein, and the carotid artery was illuminated with a 1.5 mW 540 nm laser (Melles Griot, Carlsbad, Calif.) positioned 6 cm from the artery. Flow was monitored for 1.20 minutes. Mice were sacrificed by pentobarbital overdosed after conclusion of the experiment while under anesthesia. The laser light converts the dye to free radicals which result in vessel occlusion with a platelet rich thrombus in 44.7±6.5 minutes in vehicle controls. In mice treated with SbO4L, occlusion occurred in 76±21.3 minutes, demonstrating significant anticoagulant activity.

FIG. 10A shows the formation of occlusive platelet-rich thrombus in the carotid artery of mice using a 3.5% $FeCl_3$ solution with two doses of SbO4L, i.e. 100 µg and 1,000 µg. FIG. 10B demonstrates a dose-dependent decrease in coagulation with a complete inhibition of clot formation at a dose of 1,000 µg of SbO4L. The number shown in brackets shows the fraction of mice which showed complete thrombotic plug formation.

Discussion

Despite a massive effort of the past 30 years it has been difficult to find a truly viable alternative to UFH and LMW heparins. The sulfated polysaccharides are very good at resolving thrombotic disorders, while being fairly inexpensive. Poly- or oligo-saccharide variants, e.g., idraparinux and its biotinylated forms,[39,40] fondaparinux conjoined to a direct thrombin inhibitor,[41] and heparin octasaccharides,[42] continue to be developed because of the high anticoagulant efficiency achievable with the saccharide scaffold. Yet, each variant carries a major synthetic burden that cannot be expected to match the much lower cost effectiveness of the heparins. A fundamental challenge, therefore, is to design an anticoagulant that effectively challenges heparins by affording high potency and high selectivity, promising reduced adverse effects, while being very easy to produce.

SbO4L was designed so as to achieve this objective. SbO4L can be synthesized in high yields in only three steps from an appropriately functionalized monomer. This protocol is significantly more efficient than the dozens of steps used in the synthesis of fondaparinux-related anticoagulants[39-42] as well as in the synthesis of active site directed anticoagulants, e.g., dabigatran, apixaban or rivaroxaban. In fact, the three-step protocol can be completed in a week using a simple synthetic set up, which is expected to put forth a highly cost effective solution to heparins. Process scale up should be possible. The chemistry used in the synthesis of SbO4L ensures that the oligomer is homogeneous with regard to inter-monomeric linkages. This greatly reduces the structural complexity in SbO4L in comparison to its precursor, sulfated LMW lignin,[17,19,21-25] as well as oligomeric heparins.[1,34]

SbO4L is a highly potent anticoagulant in vitro and ex vivo. SbO4L inhibits thrombin (and plasmin) with high selectivity, while inhibiting factors IXa, Xa and XIa with a potency that is orders of magnitude lower. Factor VIIa-TF complex, the physiologic extrinsic pathway initiator, is inhibited with ~10-fold lower potency, while plasma antithrombin does not affect direct action of SbO4L. Competing macromolecule TM, which alters the substrate specificity of thrombin, is likely to be functional only at ~20-times higher concentrations of SbO4L (Table 1).

The in vitro potency against thrombin (0.17 µg/ml) changes to ~20 µg/ml for doubling APTT and ~80 µg/ml for effective anticoagulation of human whole blood. The primary reason for this significant drop in anticoagulant effect in plasma and blood is likely to be non-specific binding to serum albumin. This is not unusual as nearly all drugs bind to serum proteins, especially albumin. In fact, most agents exhibit significant protein binding resulting in considerable loss in effective potency. Rather binding to serum albumin may actually be an advantage because of the possibility of a slow release mechanism. On weight basis, ~3 µg/ml enoxaparin induces a blood anticoagulation equivalent to ~80 µg/ml SbO4L suggesting that the non-saccharide anticoagulant is likely to be nearly 20-30-fold weaker in clinical efficiency. This is not necessarily a disadvantage because the more important parameter is the ratio of potency to adverse effects (bleeding, thrombocytopenia, hepatotoxicity, etc.) in vivo.

SbO4L inhibits thrombin with an efficacy of ~60%, whereas heparins have an efficacy of nearly 100% because their primary effector, antithrombin, is a covalent inhibitor of thrombin and other coagulation enzymes.[1,34] This implies that even at saturation, the SbO4L-thrombin complex is likely to display a reduced level of pro-coagulant efficacy. This is a specific advantage of allosteric inhibitors and is the reason why these molecules are called regulators. SbO4L appears to possess this advantage and suggests its use as an effective prophylactic agent.

SbO4L allostery arises from binding in exosite 2 of thrombin, which also engages polymeric heparin. Although nearly ideal competition between heparin and SbO4L is indicated by competitive inhibition studies, it is not necessary that the two ligands are strictly mutually exclusive. Exosite 2 is a fairly large area spanning ~20×30 Å$^2$ and consisting of numerous electropositive residues including Arg93, Arg101, Arg165, Arg233, Lys235, Lys236, and Lys240. Of these, polymeric heparin recognizes Lys236, Lys240, Arg93, Arg101 and Arg233.[43,44] Sulfated LMW lignins, the precursors of SbO4L, were found to bind to Arg93 and Arg175.[17] Thus, the geometries of polymeric heparin and sulfated LMW lignins in exosite 2 of thrombin appear to be significantly different. Structurally, SbO4L is more heparin-like in terms of its sulfation density, but is more LMW lignin-like in terms of its hydrophobic scaffold. Thus, it is not clear whether SbO4L binding in exosite 2 will resemble heparin or sulfated LMW lignins. Yet, this geometry will determine whether SbO4L inhibits thrombin in a fibrin-bound state.

A key advantage in the use of polymeric heparins is the availability of protamine as an antidote. SbO4L is also a sulfated polymer and its direct inhibition of thrombin is neutralized by protamine. In fact in chromogenic test systems, protamine was found to restore 100% thrombin activity with a $RC_{50}$ only 5-fold higher than $IC_{50}$. Additionally, the effect was instantaneous as no extended incubation was necessary. An average UFH chain contains nearly 1.7 anionic groups (—$OSO_3^-$ and —$COO^-$) per monosaccharide, while SbO4L contains nearly two —$OSO_3^-$ groups, which explains the highly effective protamine reversal.

Overall, the present work puts forward a novel designed sulfated β-O4 lignin molecule, SbO4L, as a highly selective and potent anticoagulant with considerable promise. SbO4L is exciting because it can be readily synthesized, is not derived from animals, is an allosteric regulator and its anticoagulation is likely to be reversed using the traditional heparin antidote, protamine.

REFERENCES

1. Henry B L, Desai U R. Anticoagulants. In: Abraham D J, Rotella D P, eds. Burger's Medicinal Chemistry, Drug Discovery and Development. Seventh Edition. Hoboken, N.J.: John Wiley; 2010:365-408.

2. Bounameaux H, Perrier A. Duration of anticoagulation therapy for venous thromboembolism. Hematology Am. Soc. Hematol. Educ. Program 2008:252-258.
3. Ryan F, Byrne S, O'Shea S. Managing oral anticoagulation therapy: improving clinical outcomes. A review. J. Clin. Pharm. Ther. 2008; 33(6):581-590.
4. van Dongen C J, van den Belt A G, Prins M H, Lensing A W. Fixed dose subcutaneous low molecular weight heparins versus adjusted dose unfractionated heparin for venous thromboembolism. Cochrane Database Syst. Rev. 2004; (4), CD001100.
5. Menajovsky L B. Heparin-induced thrombocytopenia: clinical manifestations and management strategies. Am. J. Med. 2005; 118 Suppl 8A: 21S-30S.
6. Holzheimer R G. Low-molecular-weight heparin (LMWH) in the treatment of thrombosis. Eur. J. Med. Res. 2004; 9(4):225-239.
7. Abdel-Wahab M, Richardt G. Safety of bivalirudin in patients with coronary artery disease. Expert Opin. Drug Saf. 2011; 11(1):141-150.
8. Yeh R W, Baron S J, Healy J L, et al. Anticoagulation with the direct thrombin inhibitor argatroban in patients presenting with acute coronary syndromes. Catheter Cardiovasc. Interv. 2009; 74(2):359-364.
9. Bauer K A. New anticoagulants. Hematology Am Soc Hematol Educ Program 2006:450-456.
10. Eriksson B I, Dahl O E, Huo M H, et al. RE-NOVATE II Study Group. Oral dabigatran versus enoxaparin for thromboprophylaxis after primary total hip arthroplasty (RE-NOVATE II*). A randomised, double-blind, non-inferiority trial. Thromb. Haemost. 2011; 105(4):721-729.
11. Ganetsky M, Babu K M, Salhanick S D, Brown R S, Boyer E W. Dabigatran: review of pharmacology and management of bleeding complications of this novel oral anticoagulant. J. Med. Toxicol. 2011; 7(4): 281-287.
12. Alexander D, Jeremias A. Rivaroxaban in the contemporary treatment of acute coronary syndromes. Expert Opin. Investig. Drugs 2011; 20(6):849-857.
13. Huisman M V. The proof for new oral anticoagulants: clinical trial evidence. Eur. Orthop. Traumatol. 2011; 2(1-2):7-14.
14. Kamath P, Huntington J A, Krishnaswamy S. Ligand binding shuttles thrombin along a continuum of zymogen- and proteinase-like states. J. Biol. Chem. 2010; 285(37): 28651-28658.
15. Häcker H G, Sisay M T, Gütschow M. Allosteric modulation of caspases. Pharmacol. Ther. 2011; 132(2): 180-195.
16. Hedstrom L. Serine protease mechanism and specificity. Chem. Rev. 2002; 102(12):4501-4524.
17. Abdel Aziz M H, Mosier P D, Desai U R. Identification of the site of binding of sulfated, low molecular weight lignins on thrombin. Biochem. Biophys. Res. Commun. 2011; 413(2):348-352.
18. Sidhu P S, Liang A, Mehta A Y, Abdel Aziz M H, Zhou Q, Desai U R. Rational design of potent, small, synthetic allosteric inhibitors of thrombin. J. Med. Chem. 2011; 54(15):5522-5531.
19. Henry B L, Abdel Aziz M, Zhou Q, Desai U R. Sulfated, low-molecular-weight lignins are potent inhibitors of plasmin, in addition to thrombin and factor Xa: Novel opportunity for controlling complex pathologies. Thromb. Haemost. 2010; 103(3):507-515.
20. Verghese J, Liang A, Sidhu P P, Hindle M, Zhou Q, Desai U R. First steps in the direction of synthetic, allosteric, direct inhibitors of thrombin and factor Xa. Bioorg. Med. Chem. Lett. 2009; 19(15):4126-4129.
21. Henry B L, Thakkar J N, Martin E J, Brophy D F, Desai U R. Characterization of the plasma and blood anticoagulant potential of structurally and mechanistically novel oligomers of 4-hydroxycinnamic acids. Blood Coagul. Fibrinolysis 2009; 20(1):27-34.
22. Henry B L, Monien B H, Bock P E, Desai U R. A novel allosteric pathway of thrombin Exosite II mediated potent inhibition of thrombin by chemo-enzymatic, sulfated dehydropolymers of 4-hydroxycinnamic acids. J. Biol. Chem. 2007; 282(44):31891-31899.
23. Monien B H, Henry B L, Raghuraman A, Hindle M, Desai U R. Novel chemo-enzymatic oligomers of cinnamic acids as direct and indirect inhibitors of coagulation proteinases. Bioorg. Med. Chem. 2006; 14(23):7988-7998.
24. Henry B L, Connell J, Liang A, Krishnasamy C, Desai U R. Interaction of antithrombin with sulfated, low molecular weight lignins: opportunities for potent, selective modulation of antithrombin function. J. Biol. Chem. 2009; 284(31):20897-20908.
25. Henry B L, Thakkar J N, Liang A, Desai U R. Sulfated, low molecular weight lignins inhibit a select group of heparin-binding serine proteases. Biochem. Biophys. Res. Commun. 2012; 417(1):382-386.
26. Verhamme I M, Olson S T, Tollefsen D M, Bock P E. Binding of exosite ligands to human thrombin. Re-evaluation of allosteric linkage between thrombin exosites I and II. J. Biol. Chem. 2002; 277(9):6788-6798.
27. Kishimoto T, Uraki Y, Ubukata M. Synthesis of bromoacetophenone derivatives as starting monomers for β-O-4 type artificial lignin polymers. J. Wood Chem. Tech. 2008; 28(2):97-105.
28. Kishimoto T, Uraki Y, Ubukata M. Chemical synthesis of β-O-4 type artificial lignin. Org. Biomol. Chem. 2006; 4(7):1343-1347.
29. Kishimoto T, Uraki Y, Ubukata M. Synthesis of β-O-4-type artificial lignin polymers and their analysis by NMR spectroscopy. Org. Biomol. Chem. 2008; 6(16):2982-2987.
30. Al-Horani R A, Desai U R. Chemical sulfation of small molecules—Advances and challenges. Tetrahedron 2010; 66:2907-2918.
31. Raghuraman A, Riaz M, Hindle M, Desai U R. Rapid, high-yielding microwave-assisted per-sulfation of organic scaffolds. Tetrahedron Lett. 2007; 48:6754-6758.
32. Slungaard A, Key N S. Platelet factor 4 stimulates thrombomodulin protein C-activating cofactor activity. A structure-function analysis. J Biol Chem. 1994; 269(41): 25549-25556.
33. Boerjan W, Ralph J, Baucher M. Lignin biosynthesis. Annu. Rev. Plant Biol. 2003; 54:519-46.
34. Desai U R. New antithrombin-based anticoagulants. Med Res Rev. 2004; 24(2):151-81.
35. Rezaie A R. Regulation of the protein C anticoagulant and antiinflammatory pathways. Curr Med Chem. 2010; 17(19):2059-2069.
36. Anastasiou G, Gialeraki A, Merkouri E, Politou M, Travlou A. Thrombomodulin as a regulator of the anticoagulant pathway: implication in the development of thrombosis. Blood Coagul Fibrinolysis 2012; 23(1):1-10.
37. Warkentin T E, Greinacher A, Craven S, Dewar L, Sheppard J A, Ofosu F A. Differences in the clinically effective molar concentrations of four direct thrombin inhibitors explain their variable prothrombin time prolongation. Thromb Haemost. 2005; 94(5):958-964.

38. Carr M E Jr. Development of platelet contractile force as a research and clinical measure of platelet function. Cell Biochem Biophys. 2003; 38(1):55-78.
39. de Kort M, Buijsman R C, van Boeckel C A A. Synthetic heparin derivatives as new anticoagulant drugs. Drug Disc Today 2005; 10(11):769-779.
40. Petitou M, Nancy-Portebois V, Dubreucq G, et al. From heparin to EP217609: the long way to a new pentasaccharide-based neutralisable anticoagulant with an unprecedented pharmacological profile. Thromb Haemost. 2009; 102(5):804-810.
41. Olson S T, Swanson R, Petitou M. Specificity and selectivity profile of EP217609: a new, neutralizable, dual-action anticoagulant that targets thrombin and factor Xa. Blood 2012; 119(10):2187-2195.
42. Xu Y, Masuko S, Takieddin M, et al. Chemoenzymatic synthesis of homogeneous ultralow molecular weight heparins. Science 2011; 334(6055):498-501.
43. Carter W J, Cama E, Huntington J A. Crystal structure of thrombin bound to heparin. J Biol Chem. 2005; 280(4): 2745-2749.
44. Tsiang M, Jain A K, Gibbs C S. Functional requirements for inhibition of thrombin by antithrombin III in the presence and absence of heparin. J Biol Chem. 1997; 272(18):12024-12029.
45. Fredenburgh J C, Stafford A R, Leslie B A, Weitz J I. Bivalent binding to gammaA/gamma'-fibrin engages both exosites of thrombin and protects it from inhibition by the antithrombin-heparin complex. J Biol Chem. 2008; 283 (5):2470-2477.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A SbO4L compound having a general chemical structure:

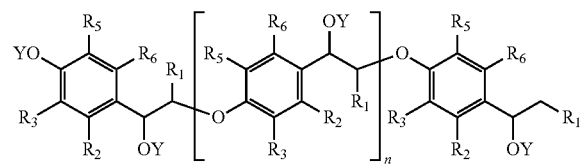

where
Y is $SO_3M$ or H, where at least one Y is $SO_3M$;
M is a positively charged ion;
n ranges from 4-30;
$R_1$ is $CH_2OY$; and
$R_2$, $R_3$, $R_5$, and $R_6$ may be the same or different and are selected from the group consisting of hydrogen, C1-10 linear alkyl, C1-10 branched alkyl, C1-10 and O1-10 oxyalkyl, an electron-donating group, and electron-withdrawing group, a halogen, —$NH_2$, and —NHR where R is selected from the group consisting of C1-10 alkyl, C1-10 aryl, C1-10 allyl, and benzyl,
and wherein a sulfation density based on a difference in $M_W$ between the SbO4L compound and its unsulfated precursor is about 2 sulfate groups per monomer.

2. The SbO4L compound of claim 1, wherein at least a plurality of Y moieties are $SO_3M$.
3. The SbO4L compound of claim 1, wherein M is independently selected from the group consisting of $Na^+$, $Ca^{2+}$, and $NH_4^+$.
4. The SbO4L compound of claim 1, wherein R1 is $CH_2OY$ in which Y is $SO_3M$.
5. A sulfated low molecular weight lignin preparation comprising the SbO4L compound of claim 1 wherein n ranges from 4-6.
6. A sulfated low molecular weight lignin preparation comprising the SbO4L compound of claim 1 wherein n ranges from 5-10.
7. A sulfated low molecular weight lignin preparation comprising the SbO4L compound of claim 1 wherein n ranges from 10-25.
8. A sulfated low molecular weight lignin preparation comprising the SbO4L compound of claim 1 wherein n ranges from 15-30.
9. A mixture of two or more different sulfated lignin scaffolds, each of which is a SbO4L compound as set forth in claim 1.
10. A lignin containing composition comprising:
one or more carriers or matrices; and
one or more lignins, at least one of which is an SbO4L compound as set forth in claim 1.
11. The SbO4L compound of claim 1 wherein the general chemical structure is

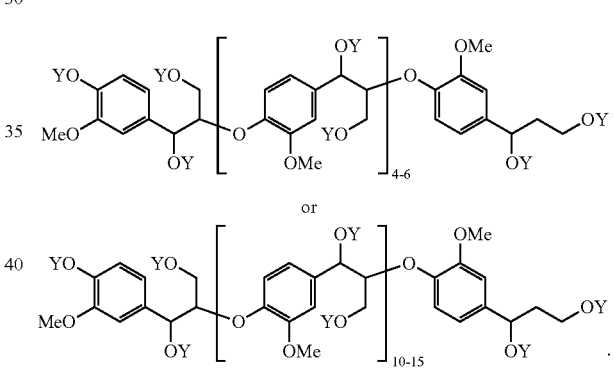

12. The SbO4L compound of claim 11, wherein at least a plurality of Y moieties are $SO_3M$.
13. A mixture of two or more different sulfated lignin scaffolds, each of which is a SbO4L compound as set forth in claim 11.
14. A lignin containing composition comprising:
one or more carriers or matrices; and
one or more lignins, at least one of which is an SbO4L compound as set forth in claim 11.
15. A method of making an SbO4L compound or mixture of SbO4L compounds as set forth in claim 1, comprising the steps of:
polymerizing at least one monomer of a beta-O4 lignin compound to obtain a polymer;
reducing the polymer produced in said polymerizing step; and
sulfating the reduced polymers produced in said reducing step to a level of about 2 sulfate groups per monomer, compared to the reduced polymers.
16. The method of claim 15, wherein said at least one monomer is ethyl 2-bromo-3-(4-hydroxy-3-methoxyphenyl)-3-oxo-propanoate.

17. The method of claim 15 wherein said at least one monomer is only one monomer.

18. A method of making an SbO4L compound or mixture of SbO4L compounds as set forth in claim 11, comprising the steps of:
- polymerizing at least one monomer of a beta-O4 lignin compound to obtain a polymer;
- reducing the polymer produced in said polymerizing step; and
- sulfating the reduced polymers produced in said reducing step to a level of about 2 sulfate groups per monomer, compared to the reduced polymers.

19. A method of preventing or reducing coagulation of blood or plasma, comprising the step of adding to said blood or plasma an SbO4L compound as set forth in claim 1 or a mixture or composition containing said SbO4L compound to said blood or plasma.

20. The method of claim 19 wherein said step of adding is performed ex vivo.

21. The method of claim 19 wherein said step of adding is performed in vivo.

22. A method of preventing or reducing coagulation of blood or plasma, comprising the step of adding to said blood or plasma an SbO4L compound as set forth in claim 11 or a mixture or composition containing said SbO4L compound to said blood or plasma.

23. The method of claim 22 wherein said step of adding is performed ex vivo.

24. The method of claim 22 wherein said step of adding is performed in vivo.

\* \* \* \* \*